US011485789B2

(12) United States Patent
Choi

(10) Patent No.: US 11,485,789 B2
(45) Date of Patent: Nov. 1, 2022

(54) MODULAR, CONTROLLED SINGLE CHAIN VARIABLE FRAGMENT ANTIBODY SWITCH

(71) Applicant: Jay H. Choi, East Windsor, NJ (US)

(72) Inventor: Jay H. Choi, East Windsor, NJ (US)

(73) Assignee: Jay H. Choi, East Windsor, NJ (US)

( * ) Notice: Subject to any disclaimer, the term of this patent is extended or adjusted under 35 U.S.C. 154(b) by 149 days.

(21) Appl. No.: 16/146,357

(22) Filed: Sep. 28, 2018

(65) Prior Publication Data

US 2019/0144551 A1 May 16, 2019

Related U.S. Application Data

(60) Provisional application No. 62/584,857, filed on Nov. 12, 2017.

(51) Int. Cl.

| | |
|---|---|
| ***C07K 16/46*** | (2006.01) |
| ***C12N 15/62*** | (2006.01) |
| ***C07K 16/28*** | (2006.01) |
| ***A61P 35/00*** | (2006.01) |
| ***C07K 16/22*** | (2006.01) |
| ***C07K 16/26*** | (2006.01) |
| ***C07K 14/00*** | (2006.01) |
| ***C07K 16/32*** | (2006.01) |

(52) U.S. Cl.

CPC .......... *C07K 16/2869* (2013.01); *A61P 35/00* (2018.01); *C07K 14/00* (2013.01); *C07K 16/22* (2013.01); *C07K 16/26* (2013.01); *C07K 16/2803* (2013.01); *C07K 16/32* (2013.01); *C07K 16/46* (2013.01); *C12N 15/62* (2013.01); *C07K 2317/622* (2013.01); *C07K 2317/70* (2013.01); *C07K 2319/32* (2013.01)

(58) Field of Classification Search

CPC combination set(s) only.
See application file for complete search history.

(56) References Cited

U.S. PATENT DOCUMENTS

2018/0319890 A1* 11/2018 Santoro ............ C07K 14/70578

OTHER PUBLICATIONS

Hu et al (BioMed Research International, Sep. 2017, article ID 8946935, 9 pages).*
Zhao et al (ACS Chem. Biol., 2018, 13:609-617; published online Jan. 8, 2018).*
Lu et al (Nucleic acids Research, 2018, 46:e25; published online Dec. 9, 2017).*
Lu et al (Nucleic acids Research, 2018, 46:e25; published online Dec. 9, 2017) Supplemental Data.*
Juillerat, Alexandre et al. "Design of chimeric antigen receptors with integrated controllable transient functions." Scientific reports vol. 6 18950. Jan. 11, 2016, doi:10.1038/srep18950.
Stein, Viktor, and Kirill Alexandrov. "Synthetic protein switches: design principles and applications." Trends in biotechnology vol. 33,2(2015): 101-10.doi:10.1016/j.tibtech.2014.11.010.
Wu, C.-Y., Roybal, K. T., Puchner, E. M., Onuffer, J., & Lim, W. A. (2015). Remote control of therapeutic T cells through a small molecule-gated chimeric receptor. Science, 350(6258), aab4011-aab4077. doi:10.1126/science.aab4077.
Ma, Jennifer S Y et al. "Versatile strategy for controlling the specificity and activity of engineered T cells." Proceedings of the National Academy of Sciences of the United States of America vol. 113,4 (2016): E450-8. doi:10.1073/pnas.1524193113.
Sadelain, Michel. "CD19 Cart Cells." Cell vol. 171,7(2017): 1471. doi:10.1016/j.cell.2017.12.002.
Guntas, Gurkan, and Marc Ostermeier. "Creation of an allosteric enzyme by domain insertion." Journal of molecular biology vol. 336,1 (2004): 263-73. doi:10 1016/j.jmb.2003.12.016.
Guntas G, Mansell TJ, Kim JR, Ostermeier M. Directed evolution of protein switches and their application to the creation of ligand-binding proteins. Proc Natl Acad Sci USA. 2005;102(32):11224-11229. doi:10.1073/pnas.0502673102.
Choi JH, San A, Ostermeier M. Non-allosteric enzyme switches possess larger effector-induced changes in thermodynamic stability than their non-switch analogs. Protein Sci. 2013;22(4):475-485. doi:10.1002/pro.2234.
Wright CM, Wright RC, Eshleman JR, Ostermeier M. A protein therapeutic modality founded on molecular regulation. Proc Natl Acad Sci USA 2011;108(39):16206-16211 doi:10.1073/pnas.1102803108.
Feil, R et al. "Ligand-activated site-specific recombination in mice." Proceedings of the National Academy of Sciences of the United States of America vol. 93,20 (1996): 10887-90. doi:10.1073/pnas.93.20.10887.
Feil, R et al. "Regulation of Cre recombinase activity by mutated estrogen receptor ligand-binding domains." Biochemical and biophysical research communications vol. 237,3 (1997): 752-7 doi:10.1006/bbrc.1997.7124.
Nicholes, N et al. "Modular protein switches derived from antibody mimetic proteins." Protein engineering, design & selection : PEDS vol. 29,2 (2016): 77-85. doi:10.1093/protein/gzv062.
Blenner MA, Banta S. Characterization of the 4D5Flu single-chain antibody with a stimulus-responsive elastin-like peptide linker: a potential reporter of peptide linker conformation. Protein Sci. 2008;17(3):527-536. doi:10.1110/ps.073257308.
Liu, Kaiwen Ivy et al. "A chemical-inducible CRISPR-Cas9 system for rapid control of genome editing." Nature chemical biology vol. 12,11 (2016): 980-987. doi:10.1038/nchembio.2179.
Dakes, Benjamin L et al. "Profiling of engineering hotspots identifies an allosteric CRISPR-Cas9 switch." Nature biotechnology vol. 34,6 (2016): 646-51. doi:10 1038/nbt.3528.

(Continued)

*Primary Examiner* — Laura B Goddard
(74) *Attorney, Agent, or Firm* — Tarolli, Sundheim, Covell & Tummino LLP

(57) ABSTRACT

A modular, small molecule regulated single chain variable fragment (scFv) fusion protein is disclosed. The scFv fusion protein comprises a ligand binding protein fused to a protein that binds to an exogenous control molecule, wherein the scFv fusion protein is directly regulated by the control molecule. Binding of the control molecule to the ligand binding protein induces a change in the affinity of the scFv for a target antigen. Methods of using the fusion protein to treat diseases such as cancer are also described.

13 Claims, 5 Drawing Sheets

Specification includes a Sequence Listing.

(56) References Cited

OTHER PUBLICATIONS

Bird, R E et al. "Single-chain antigen-binding proteins." Science (New York, N.Y.) vol. 242,4877 (1988): 423-6. doi:10.1126/science.3140379.

Huston, J S et al. "Protein engineering of antibody binding sites: recovery of specific activity in an anti-digoxin single-chain Fv analogue produced in *Escherichia coli* ." Proceedings of the National Academy of Sciences of the United States of America vol. 85,16 (1988): 5879-83. doi:10.1073/pnas.85.16.5879.

Choi, Jay H et al. "Design of protein switches based on an ensemble model of allostery." Nature communications vol. 66968 Apr. 22, 2015, doi:10.1038/ncomms7968.

Cutler, Thomas A et al. "Effect of interdomain linker length on an antagonistic folding-unfolding equilibrium between two protein domains." Journal of molecular biology vol. 386,3 (2009): 854-68. doi:10.1016/j.jmb.2008.10.090.

* cited by examiner

SEQUENCE LISTING

<160> NUMBER OF SEQ ID NOS: 13

<210> SEQ ID NO 1
<211> LENGTH: 107
<212> TYPE: PRT
<213> ORGANISM: Homo sapiens

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 2
<211> LENGTH: 119
<212> TYPE: PRT
<213> ORGANISM: Homo sapiens

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser
        115
```

<210> SEQ ID NO 3
<211> LENGTH: 236
<212> TYPE: PRT
<213> ORGANISM: Homo sapiens

<400> SEQUENCE: 3

```
Thr Ala Asp Gln Met Val Ser Ala Leu Leu Asp Ala Glu Pro Pro Ile
1               5                   10                  15

Leu Tyr Ser Glu Tyr Asp Pro Thr Arg Pro Phe Ser Glu Ala Ser Met
            20                  25                  30

Met Gly Leu Leu Thr Asn Leu Ala Asp Arg Glu Leu Val His Met Ile
        35                  40                  45
```

Asn Trp Ala Lys Arg Val Pro Gly Phe Val Asp Leu Thr Leu His Asp
    50                  55                  60

Gln Val His Leu Leu Glu Cys Ala Trp Leu Glu Ile Leu Met Ile Gly
65                  70                  75                  80

Leu Val Trp Arg Ser Met Glu His Pro Val Lys Leu Leu Phe Ala Pro
                85                  90                  95

Asn Leu Leu Leu Asp Arg Asn Gln Gly Lys Cys Val Glu Gly Met Val
            100                 105                 110

Glu Ile Phe Asp Met Leu Leu Ala Thr Ser Ser Arg Phe Arg Met Met
        115                 120                 125

Asn Leu Gln Gly Glu Glu Phe Val Cys Leu Lys Ser Ile Ile Leu Leu
    130                 135                 140

Asn Ser Gly Val Tyr Thr Phe Leu Ser Ser Thr Leu Lys Ser Leu Glu
145                 150                 155                 160

Glu Lys Asp His Ile His Arg Val Leu Asp Lys Ile Thr Asp Thr Leu
                165                 170                 175

Ile His Leu Met Ala Lys Ala Gly Leu Thr Leu Gln Gln Gln His Gln
            180                 185                 190

Arg Leu Ala Gln Leu Leu Leu Ile Leu Ser His Ile Arg His Met Ser
        195                 200                 205

Asn Lys Gly Met Glu His Leu Tyr Ser Met Lys Cys Lys Asn Val Val
    210                 215                 220

Pro Leu Tyr Asp Leu Leu Leu Glu Ala Ala Asp Ala
225                 230                 235

<210> SEQ ID NO 4
<211> LENGTH: 107
<212> TYPE: PRT
<213> ORGANISM: Homo sapiens

<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 5
<211> LENGTH: 120
<212> TYPE: PRT
<213> ORGANISM: Homo sapiens

<400> SEQUENCE: 5

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
35 40 45

Gly Val Ile Trp Gly Ser Glu Thr Thr Tyr Tyr Asn Ser Ala Leu Lys
50 55 60

Ser Arg Leu Thr Ile Ile Lys Asp Asn Ser Lys Ser Gln Val Phe Leu
65 70 75 80

Lys Met Asn Ser Leu Gln Thr Asp Asp Thr Ala Ile Tyr Tyr Cys Ala
85 90 95

Lys His Tyr Tyr Tyr Gly Gly Ser Tyr Ala Met Asp Tyr Trp Gly Gln
100 105 110

Gly Thr Ser Val Thr Val Ser Ser
115 120

<210> SEQ ID NO 6
<211> LENGTH: 470
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Thr Ala Asp Gln Met
100 105 110

Val Ser Ala Leu Leu Asp Ala Glu Pro Pro Ile Leu Tyr Ser Glu Tyr
115 120 125

Asp Pro Thr Arg Pro Phe Ser Glu Ala Ser Met Met Gly Leu Leu Thr
130 135 140

Asn Leu Ala Asp Arg Glu Leu Val His Met Ile Asn Trp Ala Lys Arg
145 150 155 160

Val Pro Gly Phe Val Asp Leu Thr Leu His Asp Gln Val His Leu Leu
165 170 175

Glu Cys Ala Trp Leu Glu Ile Leu Met Ile Gly Leu Val Trp Arg Ser
180 185 190

Met Glu His Pro Val Lys Leu Leu Phe Ala Pro Asn Leu Leu Leu Asp
195 200 205

Arg Asn Gln Gly Lys Cys Val Glu Gly Met Val Glu Ile Phe Asp Met
210 215 220

Leu Leu Ala Thr Ser Ser Arg Phe Arg Met Met Asn Leu Gln Gly Glu
225 230 235 240

Glu Phe Val Cys Leu Lys Ser Ile Ile Leu Leu Asn Ser Gly Val Tyr
245 250 255

Thr Phe Leu Ser Ser Thr Leu Lys Ser Leu Glu Glu Lys Asp His Ile
260 265 270

His Arg Val Leu Asp Lys Ile Thr Asp Thr Leu Ile His Leu Met Ala

```
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Gly Met Glu
305                 310                 315                 320

His Leu Tyr Ser Met Lys Cys Lys Asn Val Val Pro Leu Tyr Asp Leu
                325                 330                 335

Leu Leu Glu Ala Ala Asp Ala Glu Val Gln Leu Val Glu Ser Gly Gly
            340                 345                 350

Gly Leu Val Gln Pro Gly Gly Ser Leu Arg Leu Ser Cys Ala Ala Ser
        355                 360                 365

Gly Phe Asn Ile Lys Asp Thr Tyr Ile His Trp Val Arg Gln Ala Pro
    370                 375                 380

Gly Lys Gly Leu Glu Trp Val Ala Arg Ile Tyr Pro Thr Asn Gly Tyr
385                 390                 395                 400

Thr Arg Tyr Ala Asp Ser Val Lys Gly Arg Phe Thr Ile Ser Ala Asp
                405                 410                 415

Thr Ser Lys Asn Thr Ala Tyr Leu Gln Met Asn Ser Leu Arg Ala Glu
            420                 425                 430

Asp Thr Ala Val Tyr Tyr Cys Ser Arg Trp Gly Gly Asp Gly Phe Tyr
        435                 440                 445

Ala Met Asp Tyr Trp Gly Gln Gly Thr Leu Val Thr Val Ser Leu Glu
    450                 455                 460

His His His His His His
465                 470


<210> SEQ ID NO 7
<211> LENGTH: 473
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Thr Ala Asp
            100                 105                 110

Gln Met Val Ser Ala Leu Leu Asp Ala Glu Pro Pro Ile Leu Tyr Ser
        115                 120                 125

Glu Tyr Asp Pro Thr Arg Pro Phe Ser Glu Ala Ser Met Met Gly Leu
    130                 135                 140

Leu Thr Asn Leu Ala Asp Arg Glu Leu Val His Met Ile Asn Trp Ala
145                 150                 155                 160

Lys Arg Val Pro Gly Phe Val Asp Leu Thr Leu His Asp Gln Val His
                165                 170                 175
```

```
Leu Leu Glu Cys Ala Trp Leu Glu Ile Leu Met Ile Gly Leu Val Trp
            180                 185                 190

Arg Ser Met Glu His Pro Val Lys Leu Leu Phe Ala Pro Asn Leu Leu
        195                 200                 205

Leu Asp Arg Asn Gln Gly Lys Cys Val Glu Gly Met Val Glu Ile Phe
    210                 215                 220

Asp Met Leu Leu Ala Thr Ser Ser Arg Phe Arg Met Met Asn Leu Gln
225                 230                 235                 240

Gly Glu Glu Phe Val Cys Leu Lys Ser Ile Ile Leu Leu Asn Ser Gly
                245                 250                 255

Val Tyr Thr Phe Leu Ser Ser Thr Leu Lys Ser Leu Glu Glu Lys Asp
            260                 265                 270

His Ile His Arg Val Leu Asp Lys Ile Thr Asp Thr Leu Ile His Leu
        275                 280                 285

Met Ala Lys Ala Gly Leu Thr Leu Gln Gln Gln His Gln Arg Leu Ala
    290                 295                 300

Gln Leu Leu Leu Ile Leu Ser His Ile Arg His Met Ser Asn Lys Gly
305                 310                 315                 320

Met Glu His Leu Tyr Ser Met Lys Cys Lys Asn Val Val Pro Leu Tyr
                325                 330                 335

Asp Leu Leu Leu Glu Ala Ala Asp Ala Gly Glu Val Gln Leu Val Glu
            340                 345                 350

Ser Gly Gly Gly Leu Val Gln Pro Gly Gly Ser Leu Arg Leu Ser Cys
        355                 360                 365

Ala Ala Ser Gly Phe Asn Ile Lys Asp Thr Tyr Ile His Trp Val Arg
    370                 375                 380

Gln Ala Pro Gly Lys Gly Leu Glu Trp Val Ala Arg Ile Tyr Pro Thr
385                 390                 395                 400

Asn Gly Tyr Thr Arg Tyr Ala Asp Ser Val Lys Gly Arg Phe Thr Ile
                405                 410                 415

Ser Ala Asp Thr Ser Lys Asn Thr Ala Tyr Leu Gln Met Asn Ser Leu
            420                 425                 430

Arg Ala Glu Asp Thr Ala Val Tyr Tyr Cys Ser Arg Trp Gly Gly Asp
        435                 440                 445

Gly Phe Tyr Ala Met Asp Tyr Trp Gly Gln Gly Thr Leu Val Thr Val
    450                 455                 460

Ser Leu Glu His His His His His His
465                 470


<210> SEQ ID NO 8
<211> LENGTH: 477
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

-continued

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Thr
            100                 105                 110

Ala Asp Gln Met Val Ser Ala Leu Leu Asp Ala Glu Pro Pro Ile Leu
        115                 120                 125

Tyr Ser Glu Tyr Asp Pro Thr Arg Pro Phe Ser Glu Ala Ser Met Met
    130                 135                 140

Gly Leu Leu Thr Asn Leu Ala Asp Arg Glu Leu Val His Met Ile Asn
145                 150                 155                 160

Trp Ala Lys Arg Val Pro Gly Phe Val Asp Leu Thr Leu His Asp Gln
                165                 170                 175

Val His Leu Leu Glu Cys Ala Trp Leu Glu Ile Leu Met Ile Gly Leu
            180                 185                 190

Val Trp Arg Ser Met Glu His Pro Val Lys Leu Leu Phe Ala Pro Asn
        195                 200                 205

Leu Leu Leu Asp Arg Asn Gln Gly Lys Cys Val Glu Gly Met Val Glu
    210                 215                 220

Ile Phe Asp Met Leu Leu Ala Thr Ser Ser Arg Phe Arg Met Met Asn
225                 230                 235                 240

Leu Gln Gly Glu Glu Phe Val Cys Leu Lys Ser Ile Ile Leu Leu Asn
                245                 250                 255

Ser Gly Val Tyr Thr Phe Leu Ser Ser Thr Leu Lys Ser Leu Glu Glu
            260                 265                 270

Lys Asp His Ile His Arg Val Leu Asp Lys Ile Thr Asp Thr Leu Ile
        275                 280                 285

His Leu Met Ala Lys Ala Gly Leu Thr Leu Gln Gln Gln His Gln Arg
    290                 295                 300

Leu Ala Gln Leu Leu Leu Ile Leu Ser His Ile Arg His Met Ser Asn
305                 310                 315                 320

Lys Gly Met Glu His Leu Tyr Ser Met Lys Cys Lys Asn Val Val Pro
                325                 330                 335

Leu Tyr Asp Leu Leu Leu Glu Ala Ala Asp Ala Gly Gly Gly Glu Val
            340                 345                 350

Gln Leu Val Glu Ser Gly Gly Gly Leu Val Gln Pro Gly Gly Ser Leu
        355                 360                 365

Arg Leu Ser Cys Ala Ala Ser Gly Phe Asn Ile Lys Asp Thr Tyr Ile
    370                 375                 380

His Trp Val Arg Gln Ala Pro Gly Lys Gly Leu Glu Trp Val Ala Arg
385                 390                 395                 400

Ile Tyr Pro Thr Asn Gly Tyr Thr Arg Tyr Ala Asp Ser Val Lys Gly
                405                 410                 415

Arg Phe Thr Ile Ser Ala Asp Thr Ser Lys Asn Thr Ala Tyr Leu Gln
            420                 425                 430

Met Asn Ser Leu Arg Ala Glu Asp Thr Ala Val Tyr Tyr Cys Ser Arg
        435                 440                 445

Trp Gly Gly Asp Gly Phe Tyr Ala Met Asp Tyr Trp Gly Gln Gly Thr
    450                 455                 460

Leu Val Thr Val Ser Leu Glu His His His His His His
465                 470                 475
```

<210> SEQ ID NO 9
<211> LENGTH: 474

<212> TYPE: PRT
<213> ORGANISM: Homo sapiens

<400> SEQUENCE: 9

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Thr Ala Asp
            100                 105                 110

Gln Met Val Ser Ala Leu Leu Asp Ala Glu Pro Pro Ile Leu Tyr Ser
        115                 120                 125

Glu Tyr Asp Pro Thr Arg Pro Phe Ser Glu Ala Ser Met Met Gly Leu
    130                 135                 140

Leu Thr Asn Leu Ala Asp Arg Glu Leu Val His Met Ile Asn Trp Ala
145                 150                 155                 160

Lys Arg Val Pro Gly Phe Val Asp Leu Thr Leu His Asp Gln Val His
                165                 170                 175

Leu Leu Glu Cys Ala Trp Leu Glu Ile Leu Met Ile Gly Leu Val Trp
            180                 185                 190

Arg Ser Met Glu His Pro Val Lys Leu Leu Phe Ala Pro Asn Leu Leu
        195                 200                 205

Leu Asp Arg Asn Gln Gly Lys Cys Val Glu Gly Met Val Glu Ile Phe
    210                 215                 220

Asp Met Leu Leu Ala Thr Ser Ser Arg Phe Arg Met Met Asn Leu Gln
225                 230                 235                 240

Gly Glu Glu Phe Val Cys Leu Lys Ser Ile Ile Leu Leu Asn Ser Gly
                245                 250                 255

Val Tyr Thr Phe Leu Ser Ser Thr Leu Lys Ser Leu Glu Glu Lys Asp
            260                 265                 270

His Ile His Arg Val Leu Asp Lys Ile Thr Asp Thr Leu Ile His Leu
        275                 280                 285

Met Ala Lys Ala Gly Leu Thr Leu Gln Gln Gln His Gln Arg Leu Ala
    290                 295                 300

Gln Leu Leu Leu Ile Leu Ser His Ile Arg His Met Ser Asn Lys Gly
305                 310                 315                 320

Met Glu His Leu Tyr Ser Met Lys Cys Lys Asn Val Val Pro Leu Tyr
                325                 330                 335

Asp Leu Leu Leu Glu Ala Ala Asp Ala Gly Glu Val Lys Leu Gln Glu
            340                 345                 350

Ser Gly Pro Gly Leu Val Ala Pro Ser Gln Ser Leu Ser Val Thr Cys
        355                 360                 365

Thr Val Ser Gly Val Ser Leu Pro Asp Tyr Gly Val Ser Trp Ile Arg
    370                 375                 380

Gln Pro Pro Arg Lys Gly Leu Glu Trp Leu Gly Val Ile Trp Gly Ser
385                 390                 395                 400
```

```
Glu Thr Thr Tyr Tyr Asn Ser Ala Leu Lys Ser Arg Leu Thr Ile Ile
                405                 410                 415

Lys Asp Asn Ser Lys Ser Gln Val Phe Leu Lys Met Asn Ser Leu Gln
            420                 425                 430

Thr Asp Asp Thr Ala Ile Tyr Tyr Cys Ala Lys His Tyr Tyr Tyr Gly
        435                 440                 445

Gly Ser Tyr Ala Met Asp Tyr Trp Gly Gln Gly Thr Ser Val Thr Val
    450                 455                 460

Ser Ser Leu Glu His His His His His His
465                 470


<210> SEQ ID NO 10
<211> LENGTH: 478
<212> TYPE: PRT
<213> ORGANISM: Homo sapiens

<400> SEQUENCE: 10

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Thr
            100                 105                 110

Ala Asp Gln Met Val Ser Ala Leu Leu Asp Ala Glu Pro Pro Ile Leu
        115                 120                 125

Tyr Ser Glu Tyr Asp Pro Thr Arg Pro Phe Ser Glu Ala Ser Met Met
    130                 135                 140

Gly Leu Leu Thr Asn Leu Ala Asp Arg Glu Leu Val His Met Ile Asn
145                 150                 155                 160

Trp Ala Lys Arg Val Pro Gly Phe Val Asp Leu Thr Leu His Asp Gln
                165                 170                 175

Val His Leu Leu Glu Cys Ala Trp Leu Glu Ile Leu Met Ile Gly Leu
            180                 185                 190

Val Trp Arg Ser Met Glu His Pro Val Lys Leu Leu Phe Ala Pro Asn
        195                 200                 205

Leu Leu Leu Asp Arg Asn Gln Gly Lys Cys Val Glu Gly Met Val Glu
    210                 215                 220

Ile Phe Asp Met Leu Leu Ala Thr Ser Ser Arg Phe Arg Met Met Asn
225                 230                 235                 240

Leu Gln Gly Glu Glu Phe Val Cys Leu Lys Ser Ile Ile Leu Leu Asn
                245                 250                 255

Ser Gly Val Tyr Thr Phe Leu Ser Ser Thr Leu Lys Ser Leu Glu Glu
            260                 265                 270

Lys Asp His Ile His Arg Val Leu Asp Lys Ile Thr Asp Thr Leu Ile
        275                 280                 285

His Leu Met Ala Lys Ala Gly Leu Thr Leu Gln Gln Gln His Gln Arg
```

-continued

```
    290                 295                 300

Leu Ala Gln Leu Leu Leu Ile Leu Ser His Ile Arg His Met Ser Asn
305                 310                 315                 320

Lys Gly Met Glu His Leu Tyr Ser Met Lys Cys Lys Asn Val Val Pro
                325                 330                 335

Leu Tyr Asp Leu Leu Leu Glu Ala Ala Asp Ala Gly Gly Gly Glu Val
            340                 345                 350

Lys Leu Gln Glu Ser Gly Pro Gly Leu Val Ala Pro Ser Gln Ser Leu
        355                 360                 365

Ser Val Thr Cys Thr Val Ser Gly Val Ser Leu Pro Asp Tyr Gly Val
    370                 375                 380

Ser Trp Ile Arg Gln Pro Pro Arg Lys Gly Leu Glu Trp Leu Gly Val
385                 390                 395                 400

Ile Trp Gly Ser Glu Thr Thr Tyr Tyr Asn Ser Ala Leu Lys Ser Arg
                405                 410                 415

Leu Thr Ile Ile Lys Asp Asn Ser Lys Ser Gln Val Phe Leu Lys Met
            420                 425                 430

Asn Ser Leu Gln Thr Asp Asp Thr Ala Ile Tyr Tyr Cys Ala Lys His
        435                 440                 445

Tyr Tyr Tyr Gly Gly Ser Tyr Ala Met Asp Tyr Trp Gly Gln Gly Thr
    450                 455                 460

Ser Val Thr Val Ser Ser Leu Glu His His His His His His
465                 470                 475


<210> SEQ ID NO 11
<211> LENGTH: 478
<212> TYPE: PRT
<213> ORGANISM: Homo Sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Leu Gln Pro Asp
65                  70                  75                  80

Phe Ala Thr Tyr Tyr Cys Gln Gln His Tyr Thr Thr Pro Pro Thr Phe
                85                  90                  95

Gly Gln Gly Thr Lys Val Glu Ile Lys Gly Gly Gly Gly Gly Gly Thr
            100                 105                 110

Ala Asp Gln Met Val Ser Ala Leu Leu Asp Ala Glu Pro Pro Ile Leu
        115                 120                 125

Tyr Ser Glu Tyr Asp Pro Thr Arg Pro Phe Ser Glu Ala Ser Met Met
    130                 135                 140

Gly Leu Leu Thr Asn Leu Ala Asp Arg Glu Leu Val His Met Ile Asn
145                 150                 155                 160

Trp Ala Lys Arg Val Pro Gly Phe Val Asp Leu Thr Leu His Asp Gln
                165                 170                 175

Val His Leu Leu Glu Cys Ala Trp Leu Glu Ile Leu Met Ile Gly Leu
            180                 185                 190
```

-continued

```
Val Trp Arg Ser Met Glu His Pro Val Lys Leu Leu Phe Ala Pro Asn
        195                 200                 205

Leu Leu Leu Asp Arg Asn Gln Gly Lys Cys Val Glu Gly Met Val Glu
    210                 215                 220

Ile Phe Asp Met Leu Leu Ala Thr Ser Ser Arg Phe Arg Met Met Asn
225                 230                 235                 240

Leu Gln Gly Glu Glu Phe Val Cys Leu Lys Ser Ile Ile Leu Leu Asn
                245                 250                 255

Ser Gly Val Tyr Thr Phe Leu Ser Ser Thr Leu Lys Ser Leu Glu Glu
            260                 265                 270

Lys Asp His Ile His Arg Val Leu Asp Lys Ile Thr Asp Thr Leu Ile
        275                 280                 285

His Leu Met Ala Lys Ala Gly Leu Thr Leu Gln Gln Gln His Gln Arg
    290                 295                 300

Leu Ala Gln Leu Leu Leu Ile Leu Ser His Ile Arg His Met Ser Asn
305                 310                 315                 320

Lys Gly Met Glu His Leu Tyr Ser Met Lys Cys Lys Asn Val Val Pro
                325                 330                 335

Leu Tyr Asp Leu Leu Leu Glu Ala Ala Asp Ala Gly Gly Gly Gly Glu
            340                 345                 350

Val Gln Leu Val Glu Ser Gly Gly Gly Leu Val Gln Pro Gly Gly Ser
        355                 360                 365

Leu Arg Leu Ser Cys Ala Ala Ser Gly Phe Asn Ile Lys Asp Thr Tyr
    370                 375                 380

Ile His Trp Val Arg Gln Ala Pro Gly Lys Gly Leu Glu Trp Val Ala
385                 390                 395                 400

Arg Ile Tyr Pro Thr Asn Gly Tyr Thr Arg Tyr Ala Asp Ser Val Lys
                405                 410                 415

Gly Arg Phe Thr Ile Ser Ala Asp Thr Ser Lys Asn Thr Ala Tyr Leu
            420                 425                 430

Gln Met Asn Ser Leu Arg Ala Glu Asp Thr Ala Val Tyr Tyr Cys Ser
        435                 440                 445

Arg Trp Gly Gly Asp Gly Phe Tyr Ala Met Asp Tyr Trp Gly Gln Gly
    450                 455                 460

Thr Leu Val Thr Val Ser Leu Glu His His His His His His
465                 470                 475


<210> SEQ ID NO 12
<211> LENGTH: 483
<212> TYPE: PRT
<213> ORGANISM: Homo Sapiens

<400> SEQUENCE: 12

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Ser Gly Thr Asp Tyr Ser Leu Thr Ile Ser Asn Leu
65                  70                  75                  80

Glu Gln Glu Asp Ile Ala Thr Tyr Phe Cys Gln Gln Gly Asn Thr Leu
                85                  90                  95
```

-continued

```
Pro Tyr Thr Phe Gly Gly Gly Thr Lys Leu Glu Ile Thr Gly Gly Gly
            100                 105                 110

Gly Gly Gly Thr Ala Asp Gln Met Val Ser Ala Leu Leu Asp Ala Glu
        115                 120                 125

Pro Pro Ile Leu Tyr Ser Glu Tyr Asp Pro Thr Arg Pro Phe Ser Glu
    130                 135                 140

Ala Ser Met Met Gly Leu Leu Thr Asn Leu Ala Asp Arg Glu Leu Val
145                 150                 155                 160

His Met Ile Asn Trp Ala Lys Arg Val Pro Gly Phe Val Asp Leu Thr
                165                 170                 175

Leu His Asp Gln Val His Leu Leu Glu Cys Ala Trp Leu Glu Ile Leu
            180                 185                 190

Met Ile Gly Leu Val Trp Arg Ser Met Glu His Pro Val Lys Leu Leu
        195                 200                 205

Phe Ala Pro Asn Leu Leu Leu Asp Arg Asn Gln Gly Lys Cys Val Glu
    210                 215                 220

Gly Met Val Glu Ile Phe Asp Met Leu Leu Ala Thr Ser Ser Arg Phe
225                 230                 235                 240

Arg Met Met Asn Leu Gln Gly Glu Glu Phe Val Cys Leu Lys Ser Ile
                245                 250                 255

Ile Leu Leu Asn Ser Gly Val Tyr Thr Phe Leu Ser Ser Thr Leu Lys
            260                 265                 270

Ser Leu Glu Glu Lys Asp His Ile His Arg Val Leu Asp Lys Ile Thr
        275                 280                 285

Asp Thr Leu Ile His Leu Met Ala Lys Ala Gly Leu Thr Leu Gln Gln
    290                 295                 300

Gln His Gln Arg Leu Ala Gln Leu Leu Leu Ile Leu Ser His Ile Arg
305                 310                 315                 320

His Met Ser Asn Lys Gly Met Glu His Leu Tyr Ser Met Lys Cys Lys
                325                 330                 335

Asn Val Val Pro Leu Tyr Asp Leu Leu Leu Glu Ala Ala Asp Ala Gly
            340                 345                 350

Gly Gly Gly Glu Val Lys Leu Gln Glu Ser Gly Pro Gly Leu Val Ala
        355                 360                 365

Pro Ser Gln Ser Leu Ser Val Thr Cys Thr Val Ser Gly Val Ser Leu
    370                 375                 380

Pro Asp Tyr Gly Val Ser Trp Ile Arg Gln Pro Pro Arg Lys Gly Leu
385                 390                 395                 400

Glu Trp Leu Gly Val Ile Trp Gly Ser Glu Thr Thr Tyr Tyr Asn Ser
                405                 410                 415

Ala Leu Lys Ser Arg Leu Thr Ile Ile Lys Asp Asn Ser Lys Ser Gln
            420                 425                 430

Val Phe Leu Lys Met Asn Ser Leu Gln Thr Asp Asp Thr Ala Ile Tyr
        435                 440                 445

Tyr Cys Ala Lys His Tyr Tyr Tyr Gly Gly Ser Tyr Ala Met Asp Tyr
    450                 455                 460

Trp Gly Gln Gly Thr Ser Val Thr Val Ser Ser Leu Glu His His His
465                 470                 475                 480

His His His


<210> SEQ ID NO 13
<211> LENGTH: 20
<212> TYPE: PRT
```

-continued

```
<213> ORGANISM: Artificial Sequence
<220> FEATURE:
<223> OTHER INFORMATION: linker peptide

<400> SEQUENCE: 13

Gly Gly Gly Gly Ser Gly Gly Gly Gly Ser Gly Gly Gly Gly Ser Gly
1               5                   10                  15

Gly Gly Gly Ser
            20
```

MODULAR, CONTROLLED SINGLE CHAIN VARIABLE FRAGMENT ANTIBODY SWITCH

CONTINUING APPLICATION DATA

This application claims the benefit of U.S Provisional Application Ser. No. 62/584,857, filed on Nov. 12, 2017, which is incorporated by reference herein.

SEQUENCE LISTING

The instant application contains a Sequence Listing which has been submitted electronically in ASCII format and is hereby incorporated by reference in its entirety. Said ASCII copy, created on Sep. 17, 2020 is named JHC-027980 US ORD SEQUENCE LISTING_ST25 and is 35,570 bytes in size.

BACKGROUND OF THE INVENTION

In the rapidly evolving field of cancer medicine and biotherapeutics, immunotherapeutic drugs have gained worldwide acceptance as the next generation therapeutics for cancer and other related diseases in recent years. While Chimeric Antigen Receptor T-cell (CAR-T) therapy is in the most active development stage, a range of antibody-based immunotherapeutic drugs, including the recently developed immune checkpoint inhibitor therapeutics, is currently available in the market or under development. However, these immunotherapeutic drugs, especially cell-based therapeutics such as CAR-T, carry high risk of numerous fatal adverse effects and unexpected immune response. Those adverse effects include, but not limited to, tumor lysis syndrome, cytokine release syndrome, cross-reaction to kill non-tumor cell, and hyper-progression. Thus, an effective method to reduce and/or eliminate these side effects is urgently needed, and it will be the vital element of the next generation cancer immunotherapy.

For the past few years, much effort has been made in the immunotherapy, including cell-based therapy, in order to establish an effective means to control the therapeutic and side effects. Those include a kill switch, small molecule gated chimeric receptor T-cells, transient CAR T-cells, and switchable non-scFv chimeric receptors. Wu et al., Science, 350(6258):aab4077 (2015); Juillerat, A. et al. Design of chimeric antigen receptors with integrated controllable transient functions. Sci Rep., 6, 18950 (2016); Ma, J. S. et al. Proc Natl Acad Sci USA 113, E450-458 (2016). Yet, there remains a great need for an effective control mechanism and platform that can be broadly applied to existing immunotherapeutic drugs and cell-based therapies to precisely regulate therapeutic responses and efficacy, and to reduce and/or eliminate adverse effects.

Single chain variable fragment (scFv) derived from an antibody used as an extracellular component expressed on the surface of CAR T-cells. It confers antigen specificity and recognizes cancer marker such as human CD19. Sadelain, M. Cell, 171(7), 1471 (2017) A potential strategy for creating control mechanisms in CAR T platform is the use of domain insertion to couple a scFv protein and a protein that binds a desired control molecule such that the control molecule regulate the scFv's affinity for cancer antigen. In previous studies domain insertion method has been shown to be useful for creating protein switches. Stein, V. & Alexandrov, K., Trends in Biotechnology 33, 101-110 (2015). This domain insertion approach is to fuse two independent proteins create such protein switches, composed of two domains, one that has the function to be regulated (the output domain) and the other that possesses the ability to recognize the desired regulating signal (the input domain). Guntas, G. & Ostermeier, M, J Mol Biol 336, 263-273 (2004); Guntas et al., Proc Natl Acad Sci USA 102:11224-11229 (2005). Those studies have demonstrated that the domain insertion can create protein switches that function as allosteric enzymes in which binding of a small molecule to the input domain modulates the activity of the output domain via conformational changes that propagate from the input domain to the output domain. Choi et al., Protein Science 22, 475-485 (2013); Wright et al., Proc Natl Acad Sci USA 108, 16206-16211 (2011).

SUMMARY OF THE INVENTION

Generally, the presently disclosed subject matter provides a modular, controlled scFv antibody switch, the scFv antibody switch comprising a ligand binding protein fused to a protein that binds to an exogenous controlling molecule; wherein the scFv antibody switch is directly regulated by the exogenous controlling molecule.

More particularly, in some aspects, the presently disclosed subject matter uses computational design and domain insertion to convert a scFv into a modular, controlled scFv antibody switch whose ability to bind target antigen can be controlled by the FDA approved, chemotherapeutic molecule, tamoxifen and tamoxifen analogs.

Accordingly, in some aspects, the antigen binding protein comprises a single chain variable fragment targeting mammalian and human Her2 (anti-scFv-Her2) and CD19 (anti-scFv-CD19). Likewise, in some aspects, the protein that binds to an exogenous controlling molecule comprises a ligand-binding domain of the human estrogen receptor; mutated forms of the ligand-binding domain of human estrogen receptor; or a ligand-binding fragment thereof (e.g., ERT2). In such aspects, the antigen comprises mammalian and human Her2 and CD19. In such aspects, the exogenous controlling molecule comprises tamoxifen and tamoxifen analogs.

Provided herein are methods and compositions related to engineered fusion proteins comprising an input domain (e.g, a mutated form of human estrogen receptor ligand binding domain, ERT2) and an output domain (e.g., a single chain variable fragment, scFv), in which the binding of a ligand to the ERT2 domain induces a change in the affinity of the scFv for a target antigen.

Thus, in certain aspects provided herein is a fusion protein comprising an ERT2 and a scFv, wherein the scFv comprises a heavy chain immunoglobulin variable domain ($V_H$) and light chain immunoglobulin variable domain ($V_L$), wherein the binding of a ligand (e.g., a small molecule ligand such as tamoxifen or tamoxifen analogs) to the ERT2 induces a change in the affinity of the scFv for a target antigen. In certain embodiments, the ERT2 comprises a ligand-binding domain of the human estrogen receptor (ER-LBD); a mutated form of the ligand-binding domain of human estrogen receptor (e.g., ERT, ERT1, ERT2, etc.); or a ligand-binding fragment thereof. In certain embodiments, the binding of the ligand to the ERT2 increases the affinity of the scFv for the target antigen. In some embodiments, the binding of the ligand to the ERT2 reduces the affinity of the scFv for the target antigen.

In certain embodiments provided herein, the ERT2 is connected (directly or indirectly) to the N-terminus of the scFv. In some embodiments, the ERT2 is connected (directly or indirectly) to the C-terminus of the scFv. In some embodiments, the ERT2 is positioned between the VH and the VL of the scFv. In some embodiments, the scFv is positioned between subdomains of the ERT2. In some embodiments, the ERT2 sequences are separated from the scFv domain sequences by a linker (e.g., peptide linkers comprising natural and/or unnatural amino acids with or without chemical modification or a chemical linker).

In particular aspects, presently disclosed modular, controlled scFv antibody switch comprises a tamoxifen-regulated anti-Her2-scFv (Ert2H2) and tamoxifen-regulated anti-CD19-scFv (Ert2C19). In certain embodiments, the tamoxifen-regulated anti-Her2-scFv (Ert2H2) and the tamoxifen-regulated anti-CD19-scFv (Ert2C19) are selected from a protein having a sequence at least 90%, 95%, or 100% identical to any one of Ert2H2 and Ert2H2 variants, and Ert2C19 and Ert2C19 variants.

In some aspects, the presently disclosed subject matter provides a method of controlling antigen recognition of scFv in a cell, the method comprising contacting the cell with a presently disclosed modular, small molecule regulated scFv antibody switch.

In other aspects, the presently disclosed subject matter provides an antibody and antibody platform comprising a presently disclosed modular, controlled scFv antibody switch.

In certain aspects provided herein is a nucleic acid encoding a fusion protein disclosed herein. In some aspects, provided herein is a cell comprising a nucleic acid disclosed herein and/or expressing a fusion protein disclosed herein. In some certain aspects, provided herein is a pharmaceutical composition comprising a fusion protein disclosed herein. In some embodiments, provided herein are methods of treating a disease or disorder comprising administering a pharmaceutical composition disclosed herein to a subject in need thereof.

It is to be understood that both the foregoing general description and the following detailed description are exemplary and explanatory only and are not restrictive of the invention, as claimed.

BRIEF DESCRIPTION OF THE FIGURES

FIG. 4A is an illustration of an exemplary structure conformational change of the ERT2 in the absence and presence of antagonist ligand, tamoxifen, bound in ERT2 (PDB ID: 1A52 for ligand-unbound conformation and 3ERT for ligand-bound conformation). FIG. 4B shows exemplary inactive and active form of scFv models comprising of heavy ($V_H$) and light chain ($V_L$) targeting the fragment of Her2 antigen.

DETAILED DESCRIPTION OF THE INVENTION

Figure 1:
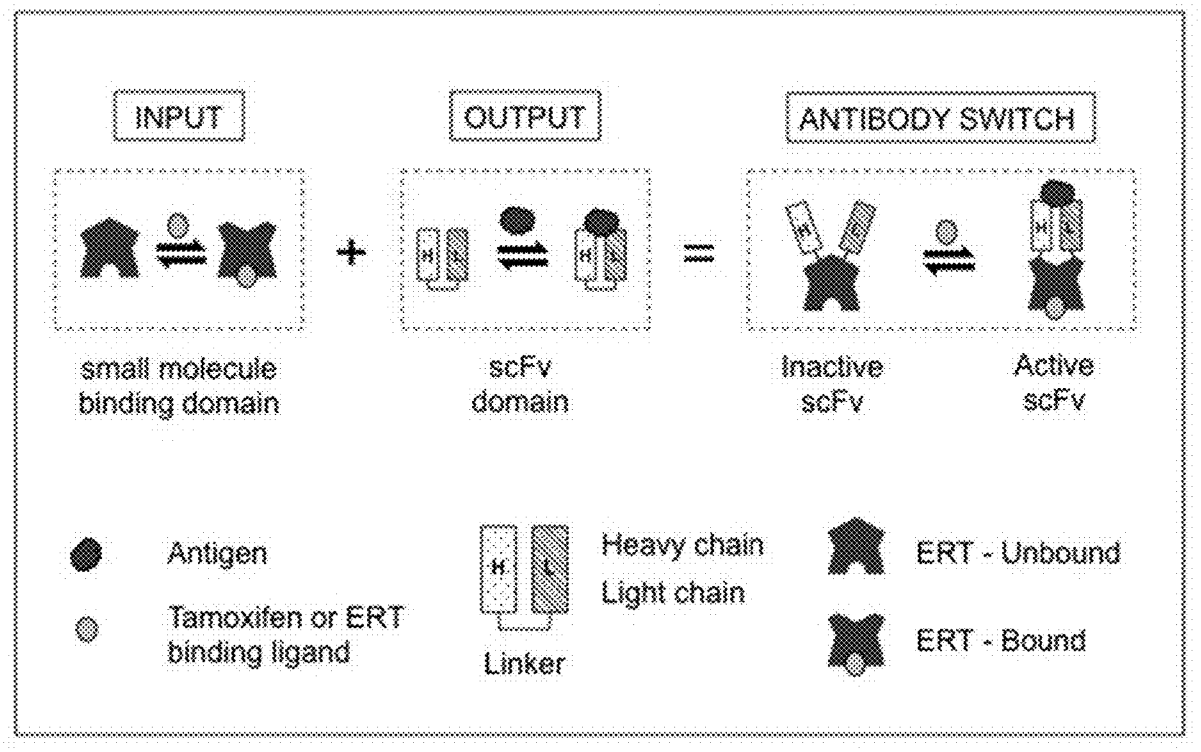
FIG. 1 provides a scheme showing an exemplary ERT2-scFv antibody switch according to certain embodiments provided herein with tamoxifen and tamoxifen analogs as an input molecule. ERT2, an input domain and scFv, an output domain are engineered to develop ERT2-scFv fusion protein switch, wherein the antigen targeting activity of the scFv domain is switched on/off or controlled in dose-dependent manner upon binding of tamoxifen to the ERT2.

The present invention provides a modular, controlled single chain variable fragment (scFv) antibody switch. The scFv antibody switch comprises a ligand binding protein fused to a protein that binds to an exogenous control molecule, wherein the scFv antibody switch is directly regulated by the control molecule. Binding of the control molecule to the ligand binding protein induces a change in the affinity of the scFv for a target antigen. Methods of using the fusion protein to treat diseases such as cancer are also provided.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

Definitions

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

As used herein, "polypeptide" refers to a polymer of amino acids and does not imply a specific length of a polymer of amino acids. Thus, for example, the terms peptide, oligopeptide, protein, antibody, and enzyme are included within the definition of polypeptide. This term also includes polypeptides with post-expression modification, such as glycosylation (e.g., the addition of a saccharide), acetylation, phosphorylation, and the like.

An "isolated" polypeptide or polynucleotide, as used herein, means a polypeptide or polynucleotide that has been either removed from its natural environment, produced using recombinant techniques, or chemically or enzymatically synthesized. Preferably, a polypeptide or polynucleotide of this invention is purified, i.e., essentially free from any other polypeptide or polynucleotide and associated cellular products or other impurities.

"Amino acid" is used herein to refer to a chemical compound with the general formula: $NH_2$—CRH—COOH, where R, the side chain, is H or an organic group. Where R is organic, R can vary and is either polar or nonpolar (i.e., hydrophobic). The following abbreviations are used throughout the application: A=Ala=Alanine, T=Thr=Threonine, V=Val=Valine, C=Cys=Cysteine, L=Leu=Leucine, Y=Tyr=Tyrosine, I=Ile=Isoleucine, N=Asn=Asparagine, P=Pro=Proline, Q=Gln=Glutamine, F=Phe=Phenylalanine, D=Asp=Aspartic Acid, W=Trp=Tryptophan, E=Glu=Glutamic Acid, M=Met=Methionine, K=Lys=Lysine, G=Gly=Glycine, R=Arg=Arginine, S=Ser=Serine, H=His=Histidine. Unless otherwise indicated, the term "amino acid" as used herein also includes amino acid derivatives that nonetheless retain the general formula.

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The term "recombinant" polynucleotide means a polynucleotide of genomic, cDNA, semisynthetic, or synthetic origin which either does not occur in nature or is linked to another polynucleotide in a non-natural arrangement.

"Substantially similar" means that a given nucleic acid or amino acid sequence shares at least 85%, more preferably at least 90%, and even more preferably at least 95% identity with a reference sequence. Furthermore, only sequences describing or encoding proteins in which only conservative substitutions are made in the conserved regions are substantially similar overall. Preferable, substantially similar sequences also retain the distinctive activity of the polypeptide. Substitutions typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

A "fusion protein," as used herein, refers to a protein having at least two heterologous polypeptides covalently linked in which one polypeptide comes from one protein sequence or domain and the other polypeptide comes from a second protein sequence or domain.

As used herein, the term "antibody switch" refers to an engineered antibody comprising an input domain that recognizes and responds to an input signal and an output domain whose function is regulated by the state of the input domain.

As used herein, an "scFv" is a single chain variable fragment of immunoglobulin or antigen receptor. A variable domain of each of the heavy ($V_H$) and light ($V_L$) chain connected in some embodiments by a multi-residue peptide linker.

As used herein, "specific binding" refers to the ability of an antibody to bind to a predetermined antigen or the ability of a ligand binding protein to bind to its predetermined control molecule. Typically, an antibody or polypeptide specifically binds to its predetermined antigen or binding partner with an affinity corresponding to a $K_D$ of about $10^{-7}$ M or less, and binds to the predetermined antigen/binding partner with an affinity (as expressed by $K_D$) that is at least 10-fold less, at least 100-fold less or at least 1000-fold less than its affinity for binding to a non-specific and unrelated antigen/binding partner (e.g., BSA, casein).

The term antigen, as used herein, refers to a molecule or a portion of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies which can be evoked by other antigens.

The term epitope, as used herein, refers to that portion of any molecule capable of being recognized by, and bound by, an antibody. In general, epitopes consist of chemically active surface groupings of molecules, for example, amino acids or sugar side chains, and have specific three-dimensional structural characteristics as well as specific charge characteristics. The epitopes of interest for the present invention are epitopes comprising amino acids.

The phrase "switching activity" refers to a measure of bioactivity difference of an antibody switch output domain in the absence and presence of an input signal that is recognized by the protein switch input domain.

A subject, as defined herein, is an animal such as a vertebrate or invertebrate organism. In some embodiments, the subject is a single celled organism such as a yeast or bacteria. In other embodiments, the subject is a mammal such as a domesticated farm animal (e.g., cow, horse, pig) or pet (e.g., dog, cat). More preferably, the subject is a human.

"Treating" a disease in a subject or "treating" a subject having a disease refers to subjecting the subject to a pharmaceutical treatment, e.g., the administration of a drug, such that at least one symptom of the disease is decreased or prevented from worsening.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

The term "ER-LBD" refers to a ligand-binding domain (LBD) of the human estrogen receptor (ESR1_HUMAN, NCBI Locus: ESR1_HUMAN, Accession: P03372). The term "ERT" includes any form of ER-LBD that comprises one or more mutations, including but not limited to truncation, addition, and deletion. Examples of ERT include ERT0 (a mutated form of ER-LBD has a single mutation: G521R), ERT1 (a mutated form of ER-LBD with triple mutations: G400V/L539A/L540A) and ERT2 (a mutated form of ER-LBD with triple mutations: G400V/M543A/L544A). Feil, R. et al., Proc Natl Acad Sci USA 93, 10887-10890 (1996); Feil, R., et al., Biochem Biophys Res Commun 237, 752-757 (1997).

scFv Fusion Proteins

In one aspect, the present invention provides a single chain variable fragment (scFv) fusion protein. The scFv protein includes an scFv comprising a heavy chain immunoglobulin variable domain ($V_H$) and a light chain immunoglobulin variable domain ($V_L$), or effective fragments thereof, and a ligand binding protein fused to the scFv, wherein the affinity of the scFv for a target antigen changes in response to binding of the receptor protein to a control molecule. The affinity of the scFv for a target antigen can change so that it exhibits either an increased or decreased affinity for the target antigen in response to binding of the ligand binding protein to a control molecule.

A protein switch is a unique biomolecular engineering method and platform that enables development of novel engineered proteins with customizable function and control of selected process. The protein switch is built from protein domains with the prerequisite effector binding (input) and functional (output) domains. These engineered proteins can have a number of exemplary properties including a large dynamic range, high specificity for the activating input signals, and a modular architecture. Thus, protein switches that can be regulated by exogenous or endogenous inputs have a broad range of biotechnological and biotherapeutics applications such as the next generation therapeutic enzymes and antibodies. One example of its application is a directed enzyme prodrug therapy. Previously, the protein switch technology has been applied to develop a therapeutic platform for the development of inherently selective protein therapeutics for cancers. Wright et al., Proc Natl Acad Sci USA 108, 16206-16211 (2011) This work introduced a synthetic biology strategy for designing protein therapeutics that autonomously activates a therapeutic function in response to a specific cancer marker of choice. It demonstrated that an engineered prodrug converting enzyme switch selectively killed human cancer cells that accumulate the marker hypoxia-inducible factor 1a. There have been many developments of engineered protein switches using protein domain such as estrogen receptor or antibody. Recently, antibody fragment or antibody mimetic forms have been used to develop protein switches. Nicholes, N. et al. Protein Eng Des Sel 29, 77-85 (2016); Blenner, M. A. & Banta, S. Protein Sci 17, 527-536 (2008). Also, switchable CRISPR-Cas9 systems have been developed, which used the ligand-binding domain of estrogen receptor protein an input domain. Liu, K. I. et al., Nat Chem Biol 12, 980-987 (2016); Oakes, B. L. et al., Nat Biotechnol 34, 646-651 (2016).

Antibody Switch for the Next Generation Immunotherapeutic Platform

Protein switch-based novel antibody switch systems, of which its antibody-antigen interaction is remotely regulated by exogenous signal such as small molecule, peptide, protein, or endogenous disease markers such as environmental signals including pH and oxidation condition, may provide an effective control mechanism for adverse effects of current immunotherapy. This versatile antibody switch platform may be used as a core molecular control component to develop an advanced, next generation immunotherapeutic platform for cell-based or antibody-based immunotherapies and biologics with a range of applications including but not limited to cancer, autoimmune diseases and other related diseases. With this novel protein switch based immunotherapeutic platform, the therapeutic activation upon specific antibody-antigen interaction may be regulated by selective, specific recognition of controlling input signal administered by a user, the physician. This remote control mechanism can be achieved by integrating the antibody switch control system into the current platform of engineered immune cell or immunotherapeutic drugs at the molecular level. This switch system may enable a control of activation mechanism, target specific antibody-antigen interaction, and fine-tuning of therapeutic activity. In CAR-T therapy, this control system may enable regulation of reaction rate and discrimination of malignant cells from normal healthy cells, and it may provide a new approach of reducing and eliminating toxicities and fatal adverse effects associated with the current generation of immunotherapy such as CAR-T therapy.

In certain aspects, an scFv fusion protein is provided which includes a ligand binding protein that functions as an input domain that interacts with a control molecule, and the scFv is an output domain that targets a target antigen. In certain embodiments, the ability of the scFv to interact with its binding antigen and targeting moiety depends upon the state of the input domain (i.e., whether the ligand binding protein is bound by a control molecule).

In certain embodiments, the antigen binding activity of scFv fusion protein, targeting its antigen, may be turned on/off or regulated in a dose-dependent manner by ligand binding interaction of the input domain with its controlling molecule as illustrated in FIG. 1.

In some embodiments, the antigen binding activity of the scFv fusion protein, targeting its antigen, may be turned on/off or regulated in a dose-dependent manner by ligand binding interaction of the ligand binding protein (i.e., input domain) with its control molecule, including but not limited to tamoxifen and its related analogs as illustrated in FIG. 1.

Single Chain Variable Fragment Fusion Proteins

In one aspect, provided herein are single chain variable fragment (scFv) fusion proteins and their corresponding DNA sequence of engineered fusion proteins. An scFv fusion protein includes an scFv comprising a heavy chain immunoglobulin variable domain ($V_H$) and a light chain immunoglobulin variable domain ($V_L$), or effective fragments thereof, and a ligand binding protein fused to the scFv, wherein the affinity of the scFv for a target antigen changes in response to binding of the ligand binding protein to a control molecule.

In some embodiments, the scFv fusion protein is connected by zero or more variable peptide linkers. Embodiments include: a) the end to end fusion of the ligand binding protein and scFv domain, b) insertion of the ligand binding protein into any position of scFv, c) insertion of the scFv into any position of the ligand binding protein, d) fusion proteins described above with any truncation, mutation, or addition of amino acid sequence within any region of the fusion proteins, and e) fusion protein of the ligand binding protein and scFv where the scFv domain can be all types of single chain variable fragment that has a general topology and architecture of variable domain of each of the heavy ($V_H$) and light chain ($V_L$), connected by variable peptide linker. In some embodiments, the ligand binding protein is fused between $V_H$ and $V_L$ of the scFv.

In some embodiments, the scFv fusion protein is substantially similar to a peptide selected from the group consisting of SEQ ID NO: 6, SEQ ID NO: 7, SEQ ID NO: 8, SEQ ID NO: 9, SEQ ID NO: 10, SEQ ID NO: 11 and SEQ ID NO: 12. These sequences are provided in Example 4, herein. An scFv fusion protein amino acid sequence that is "substantially similar" to the fusion proteins provided by sequences 6-10 will share at least 85% identity, more preferably 90% identity and even more preferably 95% identity, and will include only conservative amino acid substitutions in conserved regions.

The amount by which a given amino acid sequence is "substantially similar" to a reference sequence can be determined for example, by comparing sequence information using sequence analysis software such as the Blastp program, version 2.2.10, of the BLAST 2 search algorithm, as described by Tatusova et al. (FEMS Microbiology Letters, 174, p. 247-50 (1999)), and available on the world wide web at the National Center for Biotechnology Information website, under BLAST in the Molecular Database section. Preferably, the default values for all BLAST 2 search parameters are used, including matrix=BLOSUM62; open gap penalty=11, extension gap penalty=1, gap x_dropoff=50, expect=10, wordsize=3, and optionally, filter on. In the comparison of two amino acid sequences using the BLAST search algorithm, structural similarity is referred to as "similarity" and identity is referred to as "identity."

Amino acid identity is defined in the context of a comparison between a candidate polypeptides and a reference amino acid sequence, and is determined by aligning the residues of the two amino acid sequences (i.e., a candidate amino acid sequence and the reference amino acid sequence) to optimize the number of identical amino acids along the lengths of their sequences; gaps in either or both sequences are permitted in making the alignment in order to optimize the number of identical amino acids, although the amino acids in each sequence must nonetheless remain in their proper order.

The scFv fusion protein has a modular architecture that allows each of the input and output domain to be modified or replaced independently while it still maintains its bioactivity. This structural modularity allows modification of the input domain to change input domain properties including but not limited to ligand specificity, selectivity, binding, affinity, effective switch control concentration, and recognition of different ligand molecules. The output domain can also be modified or replaced independently such that it can recognize different target antigens with different specificity and selectivity. This modular architecture may allow develop scFv antibody switches that can regulated by a range of different input molecules and target a range of different antigens on the platform of ERT2-scFv. Ert2C19-G21 and Ert2C19-G43 constructs showed 25.7 fold and 38.3 fold switching activity respectively with 4-HT (Table 5). Thus, the scFv fusion protein provides a versatile scFv antibody platform for antigen recognition controlled by a control molecule such as tamoxifen.

Figure 2:
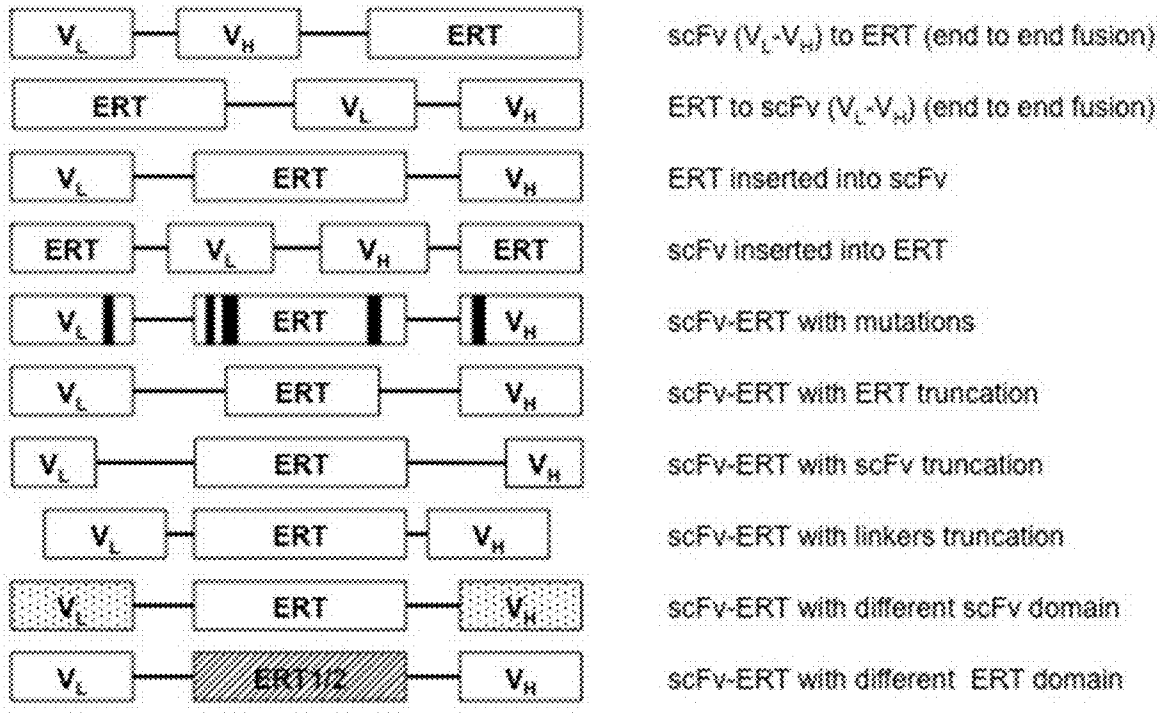
FIG. 2 provides exemplary schematics representing the DNA sequence of exemplary ERT-scFv fusions and variants thereof. Depicted are exemplary construction schemes of engineered ERT-scFv switch that involves fusion, insertion, mutation, truncation, addition, deletion of the genes that correspond to the mutated forms of ER-LBD (input domain), the scFv (output domain), and the zero or more residue linkers.
Figure 3:
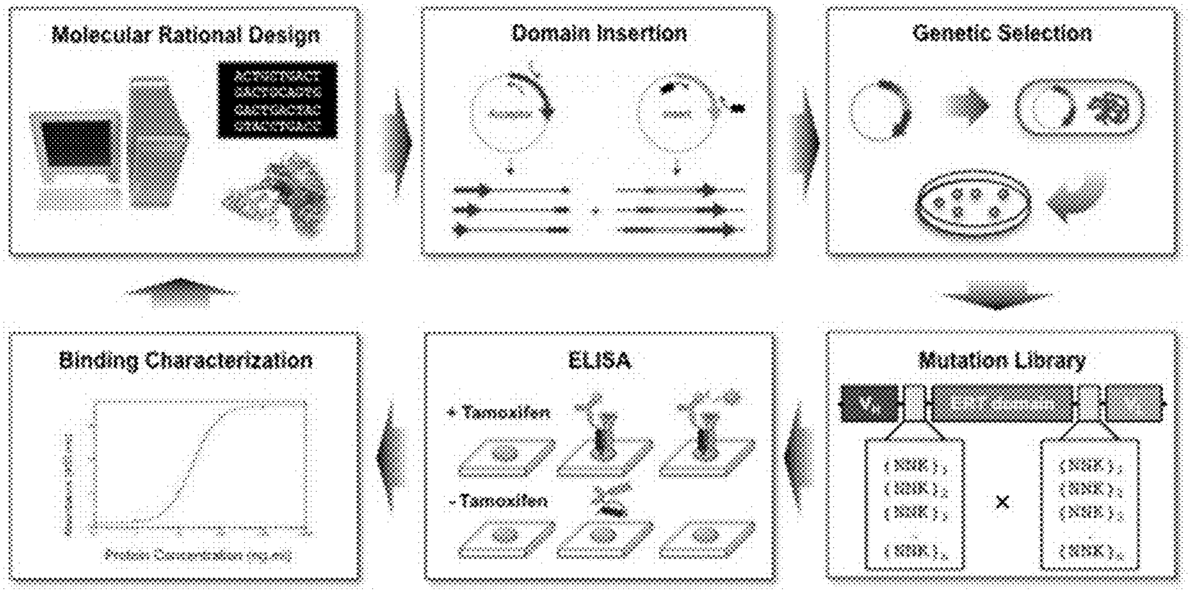
FIG. 3 provides a schematic representation of an exemplary process for engineering of ERT2-scFv antibody switch. Depicted is a general overview of the scFv antibody switch design, construction, and characterization disclosed herein. The gene constructs designed based on the computer-aided design and modeling can be subject to directed evolution library construction and mutation. The selected library gene constructs are introduced into an expression vector for production of engineered fusion proteins, and subsequently tested for small molecule dependent antigen binding activity.

In some embodiments, the scFv antibody switch platform disclosed here has a general architecture that comprises a ligand-binding input domain and an antigen-targeting scFv output domain. The input domain may be small molecule binding protein, peptide binding protein, or protein binding protein domain while the output domain may be any scFv fragment that has a general topology of heavy and light chain. In some embodiments, scFv fusion protein includes fusion, insertion, mutation, truncation, addition, deletion of the genes that correspond to the ligand binding protein (e.g., ERT2) and scFv domains, and the linker, as illustrated in FIG. 2.

In certain aspects, disclosed herein are compositions for engineered fusion proteins of an ERT2 and scFv domain that selectively activates (i.e., increases) or deactivates (i.e., decreases) the antigen targeting activity of the scFv domain with a control molecule such as tamoxifen and its analogs. This tamoxifen-controlled scFv antibody switch may provide an effective remote control mechanism that can be used for antibody based and cell based immunotherapy such as CAR-T cell therapy.

In some aspects, disclosed herein are ERT2-scFv antibody switch systems, wherein the engineered fusion proteins, ERT2-scFv comprises a ligand binding protein (e.g., ERT2) that binds to its input ligands including but not limited to tamoxifen and its related analogs and an output domain (scFv), of which its antigen target binding ability is regulated by the state of the ligand binding protein upon binding of a suitable control molecule.

In another aspect, the scFv fusion protein has externally controlled antigen binding activity. ERT2-scFv has two structural/functional domains: a) an input domain (ERT2) that recognize its input signal molecules such as tamoxifen, and its related analogs, and b) an output domain (scFv) that has specific recognition to its antigen. In ERT2-scFv, the output function, target antigen binding of the scFv, is regulated by the state of the input domain upon binding of controlling input molecules in the ERT2 domain. The bioactivity of ERT2-scFv is determined by changes of the output function (antigen binding ability and affinity by the scFv domain) by the state of the input domain (ERT2), upon binding of input molecules, and it is referred to as switching activity, the switching fold between the output functional activity in the absence and presence of input molecules. The antigen binding activity of ERT2-scFv is modulated by controlling input molecules such as tamoxifen and its related analogs, in dose dependent manner Ert2H2 showed 4-HT-dose-dependent Her2 binding activity with 10.7 fold change in activity in the absence and presence of the ligand (Table 2) while the known agonist, β-estradiol, did not show any effect on Her2 binding (Table 3).

The scFv Domain

Figure 4A:
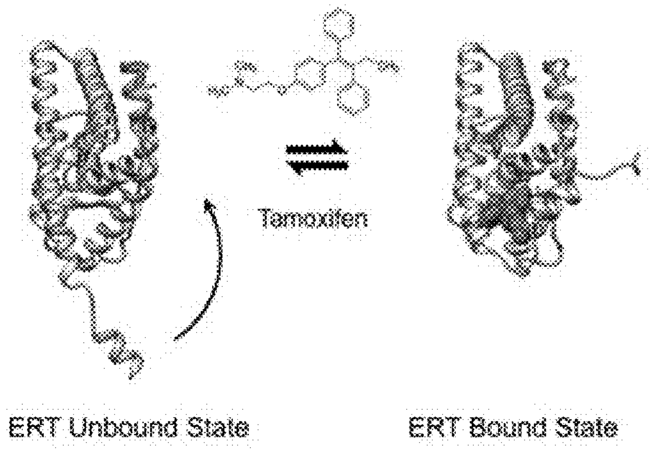
FIGS. 4A and 4B provides images showing exemplary structure models of ERT2 and scFv.
Figure 4B:
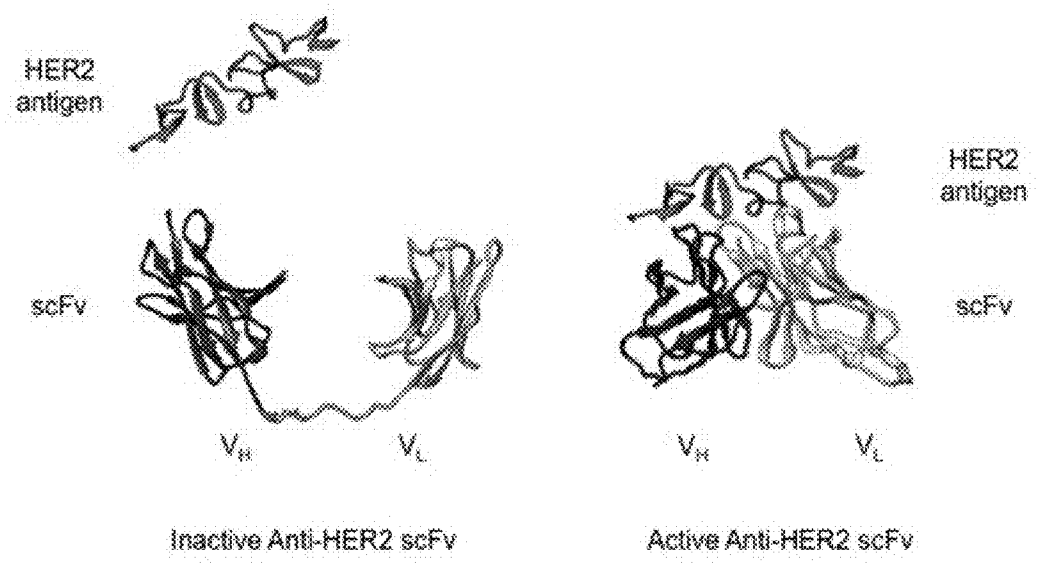

The scFv fusion protein includes an scFv domain (i.e., protein region). Single chain Fv molecules include a $V_H$ domain and a $V_L$ domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), The scFv domain may be a single chain variable fragment from all classes of immunoglobulin, T cell receptor, and B cell receptors that adapt a general topology and architecture of variable domain of each of the heavy ($V_H$) and light ($V_L$) chain connected by a multi-residue variable peptide linker, as illustrated in FIG. 4.

Structural and functional properties of the scFv including antigen-binding affinity are largely dependent on conformational states of light ($V_L$) and heavy ($V_H$) chain of the scFv, connected by a flexible linker. The antigen-binding site resides on the surface formed by dimerization of $V_L$ and $V_H$ chains, and a correct dimerization of a functionally active scFv depends on structural constraints of the connecting peptide linker including the length, flexibility, and solubility. The common linker used for the scFv is serine-glycine rich repeat peptide. The polar side chain of serine may increase solubility and stability for the structure while their small side chains provides flexibility and prevent possible steric hindrance. ERT2-scFv antibody switch can use both the serine or glycine rich repeat peptide and more rigid peptide comprising large, charged residues such glutamic acid, lysine, and arginine. Antigen binding assay showed two and four glycines in the N-terminal linker and one and three glycines in the C-terminal linker with one residue difference between linkers showed increased ligand-dependent switch ratio from 10.7 fold to 34.8 fold for Ert2H21 and 55.1 fold for Ert2H43 (see Table 4). In addition, ERT2-scFv switch may use specialized linkers such as temperature-induced, redox-induced, and pH-induced peptide, previously developed for multi-input protein switches. Choi et al., Nat Commun 6, 6968 (2015).

The scFv domain may be a single chain variable fragment that targets its natural or known antigens. The scFv domain "specifically binds" to a target antigen. A wide variety of antigens are known and can be readily identified by one skilled in the art. In some embodiments, the target antigen selected from, by non-limiting example, CD19, Her2, IgE, CLL-1, CD33, EGFRvIII, CD20, CD22, BCMA or a fragment or variants that contains mutations thereof. In some embodiments, the scFv domain is configured to specifically bind to a tumor-associated antigen.

In further embodiments, the scFv domain may be a single chain variable fragment that targets an antigen selected from CD19, Her2, or any related antigen and a fragment thereof. The antigen may comprise a wild-type, engineered, or synthetic antigen. The antigen may comprise one or more mutations. In some embodiments, the target antigen comprises Her2 or CD19.

As used herein, a "tumor-associated antigen" comprises any antigen produced by a tumor cell. A "tumor-associated antigen" can be an antigen present only in a tumor cell and not on any other cell, or it may be an antigen present in some tumor cells and also in some normal cells. Tumor-associated antigens can include, for example, products of mutated oncogenes and tumor suppressor genes, overexpressed or aberrantly expressed cellular proteins, tumor antigens produced by oncogenic viruses, oncofetal antigens, altered cell surface glycolipids and glycoproteins or cell-type specific differentiation antigens.

Various antigens (e.g., tumor-associated antigens, microbial antigens) or antigenic portions thereof can be selected for use as antigens of interest from among those antigens known in the art or determined by immunoassay to be able to bind to antibody or MHC molecules (antigenicity) or generate an immune response (immunogenicity) as described above. Additional, useful antigens or derivatives thereof can also be identified by various criteria, such as the antigen's involvement in cancer, (Norrby (1985) Vaccines 85, Lerner, et al. (eds.), Cold Spring Harbor Laboratory, Cold Spring Harbor, N.Y., pp. 388-389), type or group specificity, recognition by patients' antisera or immune cells, and/or the demonstration of protective effects of antisera or immune cells specific for the antigen.

While any antigen of interest can be employed in the methods and compositions provided herein, non-limiting examples include tumor-associated antigens or antigenic portions thereof that are associated with, derived from, or predicted to be associated with a cancer. In such instances the tumor-associated antigen of interest can be from any type of cancer, including, but not limited to, adenocarcinoma, hepatoblastoma, sarcoma, glioma, glioblastoma, neuroblastoma, plasmacytoma, histiocytoma, melanoma, adenoma, myeloma, bladder cancer, brain cancer, squamous cell carcinoma of the head and neck, ovarian cancer, skin cancer, liver cancer, lung cancer, colon cancer, cervical cancer, breast cancer, renal cancer, esophageal carcinoma, head and neck carcinoma, testicular cancer, colorectal cancer, prostatic cancer, and pancreatic cancer, or any antigenic portion thereof. In some embodiments, the tumor-associated antigen is a glioblastoma-associated antigen. In some embodiments, the tumor-associated antigen is one found on the cancer being treated.

Many types of tumor cells express antigens that are not found in normal cells. These antigens, known as tumor-associated antigens, have been intensively studied as targets for therapeutic anti-cancer vaccines. Exemplary tumor-associated antigens are lymphocyte antigen 6 complex, locus K (LY6K), cell division cycle associated 1 (CDCA1), insulin-like growth factor-II mRNA-binding protein 3 (IMP-3), kinesin family member 20A (KIF20A), glypican-3(GPC3), forkhead box M1 (FOXM1), cadherin 3 (CDH3), secreted protein acidic and rich in cysteine (SPARC), cell division cycle 45 ligand (CDC45L), DEP domain containing 1 (DEPDC1), M-phase phosphoprotein 1 (MPHOSPH1), prostate-specific antigen (PSA), prostate-specific membrane antigen (PSMA), human epidermal growth factor receptor2/neuroblastoma (HER2/neu), carcinoembryonic antigen (CEA), mutated epidermal growth factor receptor (EGFR), melanoma antigen (MAGE), mucin-1 (MUC-1), and New York esophageal squamous cell carcinoma 1 (NY-ESO-1), BAGE, GAGE, MAGE, NY-ESO-1, SSX, gp100, Melan-A/Mart-1, Tyrosinase, Mammaglobin-A, p53, livin, survivin, β-Actin/4/m, Myosin/m, HSP70-2/m, HLA-A2-R17OJ, GM2, GD2, GD3, MUC-1, sTn, globo-H, WT1, PR1, E75, ras, AFP, URLC10, VEGFR1 and 2, mutant p53, NY-ESO-1, HPV16 E7, β-catenin, CDK4, CDC27, α-actinin-4, TRP1/gp75, TRP2, gangliosides, WT1, EphA2, EphA3, CD20, telomerase, MART-1, or an antigenic portion thereof. See Hirayama et al. 2016, Int. Immunol. Advance Access May 28 pp 1-26. In some embodiments, the tumor-associated antigen is EphA2.

Specific examples of $V_L$ and $V_H$ proteins are described herein. In one embodiment, $V_L$ and $V_H$ provide a scFv that specifically binds to Her2 wherein $V_L$ comprises a polypeptide that is substantially similar to the amino acid sequence DIQMTQSPSSLSASVGDRVTITCRASQDVNTAVAWYQQKPGKAPKLLIYSASFLYSG VPSRFSGSRSGTDFTLTISSLQPEDFATYYCQQHYTTPPTFGQGTKVEIK (SEQ ID NO: 1) and $V_H$ comprises a polypeptide that is substantially similar to the amino acid sequence EVQLVESGGGLVQPGGSLRLSCAASGFNIKDTYIHWVRQAPGKGLEWVARIYPTNG YTRYADSVKGRFTISADTSKNTAYLQMNSLRAEDTAVYYCSRWGGDGFYAMDYW GQGTLVTVS (SEQ ID NO: 2).

In another embodiment, $V_L$ and $V_H$ provide a scFv that specifically binds to CD19 wherein $V_L$ comprises a polypeptide that is substantially similar to the amino acid sequence DIQMTQTTSSLSASLGDRVTISCRASQDISKYLNWYQQKPDGTVKLLIYHTSRLHSGV PSRFSGSGSGTDYSLTISNLEQEDIATYFCQQGNTLPYTFGGGTKLEIT (SEQ ID NO: 4) and $V_H$ comprises a polypeptide that is substantially similar to the amino acid sequence EVKLQESGPGLVAPSQSLSVTCTVSGVSLPDYGVSWIRQPPRKGLEWLGVIWGSETT YYNSALKSRLTIIKDNSKSQVFLKMNSLQTDDTAIYYCAKHYYYGGSYAMDYWGQ GTSVTVSS (SEQ ID NO: 5).

Ligand Binding Proteins

The scFv fusion protein also includes a ligand binding protein, which is fused to the scFv protein. The ligand binding protein specifically binds to a control molecule. Binding of the control molecule to the ligand binding protein changes the affinity of the scFv for a target antigen. wherein the ligand binding protein is a small molecule binding protein. In some embodiments, the affinity of the scFv protein for the target antigen increases in response to binding of the ligand binding protein to its corresponding control molecule. In other embodiments, the affinity of the scFv for the target antigen decreases in response to binding of the ligand binding protein to its corresponding control molecule. The degree of the increase or decrease can differ for different scFv fusion protein embodiments. In some embodiments, binding to the control molecule causes a 10% increase or decrease, a 20% increase or decrease, a 30% increase or decrease, a 40% increase or decrease, a 50% increase or decrease, a 60% increase or decrease, a 70% increase or decrease, an 80% increase or decrease, a 90% increase or decrease, or a 100% increase or decrease of the affinity of the scFv protein for the target antigen. In further embodiments, binding of the ligand binding protein to the control molecule increases the affinity of the scFv protein for the target antigen by 125%, 150%, 200%, 300%, 400%, 500%, or by more than 1000%.

The ligand binding protein can be selected to specifically bind to a wide variety of control molecules, which are known to those skilled in the art. In some embodiments, the ligand binding protein is an estrogen receptor ligand binding domain (ER-LBD) or tamoxifen-binding estrogen receptor ligand binding domain mutant (ERT-LBD), which are mutated forms of the estrogen receptor ligand binding domain that interact with estrogen and related analogs as agonists, tamoxifen and its related analogs as antagonists, and any other suitable synthetic ligands.

In certain embodiments, the ligand binding protein is an ERT2 domain. ERT2 domain includes a native ligand binding domain of estrogen receptor (ER-LBD) and its mutated forms. ERT0, ERT1, and ERT2 are mutated forms of ER-LBD that only bind antagonist molecules such as tamoxifen and its related analogs but not the agonist such as estrogen. Feil, R. et al., Proc Natl Acad Sci USA 93, 10887-10890 (1996). ER-LBD and its mutated forms have previously shown larger conformational change upon binding of their antagonist (tamoxifen related analogs) than binding of their agonist (estrogen hormone). Feil et al., Biochem Biophys Res Commun 237, 752-757 (1997); Metzger et al., Proc Natl Acad Sci USA 92, 6991-6995 (1995). As it was demonstrated in a number of different protein switch systems, the conformational change upon ligand binding of the ERT2 domain may induce conformational change of the scFv domain in the ERT2-scFv antibody switch system such that it activates or deactivates target antigen binding, described as externally controlled antigen binding activity. Ostermeier, M. Curr Opin Struct Biol 19, 442-448 (2009); Ribeiro et al., Methods Mol Biol 1596, 43-55 (2017). In ERT2-scFv switch, an unbound conformation state of the ERT2 domain may disrupt an active scFv domain due to its steric and distance constraint of the connecting linkers between the ERT2 and scFv domain. Upon tamoxifen binding, the large conformational change in the ERT2 domain may relieve the constraints and restore a native-like conformation of the scFv domain to form antigen-binding site and activate the target antigen binding.

In some embodiments, the ligand binding protein is an ERT-LBD polypeptide that is substantially similar to the amino acid sequence TADQMVSALLDAEPPILYSEYDP-TRPFSEASMMGLLTNLADRELVHMINWAKRVPG FVDLTLHDQVHLLECAWLEILMIGLVWRSMEHPV-KLLFAPNLLLDRNQGKCVEGM VEIFDMLLATSSR-FRMMNLQGEEFVCLKSIILLNSGVYTFLSSTLKSLEE-KDHIHRVLD KITDTLIHLMAKAGLTLQQQHQR-LAQLLLILSHIRHMSNKGMEHLYSMKCKNVVPL YDLLLEAADA (SEQ ID NO: 3).

Linker Peptides

In some embodiments, the scFv fusion protein includes one or more amino acid linkers connecting a scFv and a ligand binding protein may be peptide linkers comprising natural and unnatural amino acids with or without chemical modification. In some embodiments, the scFv fusion protein includes a linker peptide positioned between the scFv protein and the ligand binding protein. By "positioned between," it is meant that the linker peptide is connected by a chemical linkage (e.g., an amide linkage) to the N or C terminal of each of the scFv protein and the ligand binding protein, as described in regard to fusion proteins herein. For example, the linker peptide can be connected through an amide linkage to the C terminal region of the scFv protein and the N terminal region of the ligand binding protein.

Relatively short polypeptides are preferred for use as linker peptides. For example, linker peptides can include from 1 to 20 amino acids. Linker peptides can also include from 1 to 15, from 1 to 10, from 1 to 5, or from 3 to 5 amino acids. Examples of specific sequences that can be used as linker peptides include individual amino acids, dipeptides, tripeptides, tetrapeptides, and pentapeptides formed of glycine amino acids.

Control Molecules for the scFv Antibody Switch

The affinity of the scFv fusion protein changes in response to binding of the ligand binding protein to a control molecule. The control molecule may be a natural or synthetic ligand that binds to a ligand binding protein. The ligand can be another protein or biochemical factor such as a cytokine or hormone, or it can be a small organic molecule such as a therapeutic agent. Preferably, the control molecule is a molecule for which there is a known receptor which can be used as the ligand binding protein.

Examples of therapeutic agents include cardiovascular drugs (e.g., antihypertensive drugs, antiarrhythmic agents, and diuretics), neuropharmaceuticals (e.g., analgesics, anesthetics, and antipsychotics), gastrointestinal drugs (e.g., antiulcer drugs, antiemetics, and gastroprokinetic agents), respiratory tract agents (e.g., anthasthamtic or antiallergic drugs), antiinfective agents (antibiotics, antimycotics, and antiviral agents), endocrine-affecting drugs (e.g., steroids, hormones, and contraceptives), anti-inflammatory drugs, immunosuppressant drugs, and antitumor agents.

More specific examples of therapeutic agents include Examples of small molecule antitumor agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin a, rapamycin, thapsigargin, and bikunin, and derivatives (as defined for imaging agents) thereof.

In some embodiments, the control molecule is tamoxifen or a tamoxifen analog. Analogs, as used herein, are compounds have a structurally similar backbone (e.g., tamoxifen) but differ at a particular chemical moiety. Alcohols and esters represent analogs, differing in the presence of a hydrogen and an alkyl group. For the different moiety, there should be the expectation by one skilled in the art that substituting one moiety for another would likely result in a compound having similar properties.

The tamoxifen controlled single chain variable fragment (scFv) systems disclosed herein are an attractive option for developing more effective CAR-T with an advanced control mechanism. Unlike other previously developed control system for CAR-T, the tamoxifen controlled scFv switch system maintains its original chimeric antigen receptor platform of CAR-T that has already proven effective anti-cancer activity, but only improves the system by integrating a control component to its existing scFv in the antigen receptor domain of CAR-T. In addition, tamoxifen itself is an FDA-approved, anti-cancer drug. This strategy avoids radical change of conventional working design platform of CAR-T; thus, it reduces potential risk of having unwanted immunogenic response.

Molecular Modeling

Figure 5:
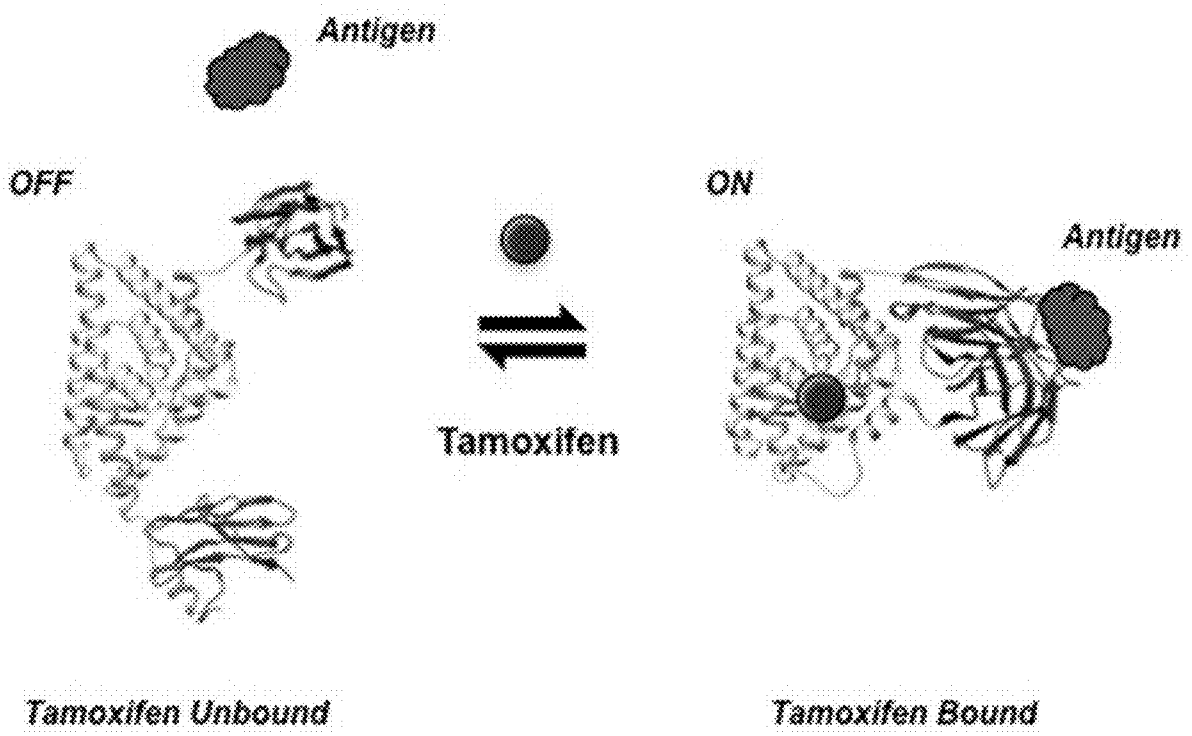
FIG. 5 provides a schematic representation of an exemplary tamoxifen regulated target antigen binding of ERT2-scFv. Illustrated is a computer designed structural models of ERT2-scFv fusion (on/off state) for antigen binding activity in the absence and presence of tamoxifen.

In some embodiments, molecular modeling is used to design the scFv fusion protein. For example, molecular modeling may be used to design fusion protein constructs of an ERT2 and a scFv domain with linkers connecting two domains in such a way that the conformational change upon ligand binding of the ERT2 domain may trigger conformational change of the scFv domain to transform from an inactive to an active form to bind target antigen. The molecular modeling demonstrates that target antigen binding of the scFv domain of ERT2-scFv fusion protein is modulated to be turned on/off upon tamoxifen binding to the ERT2 domain and its subsequent conformational change (FIG. 5). The difference in antigen binding affinity in the absence and presence of tamoxifen may be used to determine protein switch activity of ERT2-scFv fusion protein. For ERT2-scFv fusion protein, in the absence of tamoxifen, the ERT2 domain is in unbound conformational state and subsequently; the scFv domain will be in inactive form with disrupted binding site for its target antigen. In the presence of tamoxifen, conformational change triggered by allosteric regulation upon tamoxifen binding in the ERT2 domain may cause conformational change of the scFv to restore its binding site for its target antigen and increase its target affinity. This protein switch mechanism based on conformational changes of an input and output domain has previously been demonstrated in multiple systems. Wright et al., Proc Natl Acad Sci USA 108, 16206-16211 (2011); Choi et al., Nat Commun 6, 6968 (2015). Molecular modeling and simulation of ERT2-scFv indicates that an allosteric regulation upon ligand binding of the input domain and its subsequent conformational change of the output domain may be a key mechanistic element of tamoxifen-controlled target antigen binding of ERT2-scFv fusion protein.

Preparation of scFv Fusion Proteins

In certain embodiments, provided herein is a description of gene construction, protein production, and characterization of scFv fusion proteins. The genes for ERT2-scFv fusion proteins are constructed based on molecular modeling results of the ERT2 and scFv domain. The genes are commercially synthesized and cloned into a multiple cloning site of the commercially available bacterial plasmid vector. Alternatively, ERT2-scFv is inserted into the multiple cloning site, located upstream of His-Tag sequence such that the resulting gene product contains ERT2-scFv with C-terminal His-Tag for Ni-NTA purification. For production and characterization of ERT2-scFv fusion proteins, the constructed genes are over-expressed in commercially available bacterial expression system and purified. Alternatively, the genes may be cloned into eukaryotic expression vectors of yeast, baculovirus, or mammalian expression system for high yield production of proteins. ELISA is conducted to determine target antigen binding affinity under conditions with varying concentration of tamoxifen or tamoxifen analogs for tamoxifen regulated antigen binding activity of ERT2-scFv fusions.

An expression vector containing an scFv fusion protein-encoding nucleic acid molecule may be used for high-level expression of scFv fusion protein in a recombinant host cell. Expression vectors may include, but are not limited to, cloning vectors, modified cloning vectors, specifically designed plasmids or viruses. A variety of expression vectors may be used to express recombinant scFv fusion protein sequences in appropriate cell types. For example, bacterial vectors, mammalian vectors, fungal vectors, and insect vectors may be used for expression in bacteria, mammalian cells, fungal cells, and insect cells, respectively.

scFv fusion protein can be prepared by obtaining a nucleotide sequence capable of expressing an scFv fusion protein and then expressing that nucleotide sequence in a host cell. The scFv fusion protein expressed by the host cell can then be purified using a variety of techniques known to those skilled in the art, depending in part on the nature of the host cell. Nucleotide sequences capable of expressing scFv fusion proteins of the invention can be prepared using a variety of methods known to those skilled in the art.

The present invention also relates to host cells transformed or transfected with vectors comprising a nucleic acid molecule capable of expressing an scFv fusion protein. Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *Drosophila* and silkworm derived cell lines. Such recombinant host cells can be cultured under suitable conditions to produce an scFv fusion protein or a biologically equivalent form. As defined herein, the term "host cell" is not intended to include a host cell in the body of a transgenic human being, human fetus, or human embryo.

As noted above, an expression vector containing DNA encoding an scFv fusion protein may be used for expression of an scFv fusion protein in a recombinant host cell. Therefore, another aspect of this invention is a process for expressing an scFv fusion protein in a recombinant host cell, comprising: (a) introducing a vector comprising a nucleic acid comprising a sequence of nucleotides that encodes a scFv fusion protein into a suitable host cell, wherein the scFv fusion protein comprises an scFv protein, or effective fragments thereof, and a ligand binding protein fused to the scFv, and (b) culturing the host cell under conditions which allow expression of the scFv fusion protein. The scFv fusion protein can be varied to include any of the features described herein, such as the inclusion of a linker peptide connecting the scFv protein and the ligand binding protein.

Following expression of a scFv fusion protein in a host cell, the scFv fusion protein may be recovered to provide purified scFv fusion protein. Several protein purification procedures are available and suitable for use. Recombinant protein may be purified from cell lysates and extracts by various combinations of, or individual application of salt fractionation, ion exchange chromatography, size exclusion chromatography, hydroxylapatite adsorption chromatography and hydrophobic interaction chromatography. The use of affinity tags in some embodiments of the invention can facilitate purification of the protein. For example, the scFv fusion protein can be separated from other cellular proteins by use of an immunoaffinity column made with monoclonal or polyclonal antibodies specific for any portion of the scFv fusion protein.

The nucleic acids capable of expressing an scFv fusion protein may be assembled into an expression cassette which comprises sequences designed to provide for efficient expression of the fusion protein in a host cell. The cassette preferably contains an scFv fusion protein-encoding open reading frame, with related transcriptional and translations control sequences operatively linked to it, such as a promoter, and termination sequences.

In one aspect, the present invention provides a nucleic acid encoding a single chain variable fragment (scFv) fusion protein, comprising an scFv comprising a heavy chain immunoglobulin variable domain ($V_H$) and a light chain immunoglobulin variable domain ($V_L$), or effective fragments thereof, and a ligand binding protein fused to the scFv, wherein the affinity of the scFv for a target antigen changes in response to binding of the receptor protein to a control molecule. In some embodiments, the nucleic acid encodes a fusion protein that has at least 90% sequence identity to a peptide selected from the group consisting of SEQ ID NO: 6, SEQ ID NO: 7, SEQ ID NO: 8, SEQ ID NO: 9, SEQ ID NO: 10, SEQ ID NO: 11, and SEQ ID NO: 12.

With regard to protein preparation from nucleotide sequences, it is noted that a "triplet" codon of four possible nucleotide bases can exist in over 60 variant forms. Because these codons provide the message for only 20 different amino acids (as well as transcription initiation and termination), some amino acids can be coded for by more than one codon, a phenomenon known as codon redundancy. Accordingly, the nucleotide sequences used to prepare the particular amino acid sequences of scFv fusion proteins can vary considerably, depending on the particular codons used. For reasons not completely understood, alternative codons are not uniformly present in the endogenous DNA of differing types of cells, and there exists a natural hierarchy or "preference" for certain codons in certain types of cells. Accordingly, in some embodiments the choice of codons used to express an scFv fusion protein may be optimized through use of particular codons to result in higher levels of expression.

In accordance with this invention, the scFv fusion protein expression cassette is inserted into a vector. The vector is preferably a plasmid or adenoviral vector, although linear DNA linked to a promoter, or other vectors, such as adeno-associated virus or a modified vaccinia virus, retroviral or lentiviral vector may also be used. In particular, the use of *E. coli* plasmid vectors is preferred.

Disease Treatment Using scFv Fusion Proteins

Another aspect of the invention provides a method of treating a disease or disorder comprising administering a therapeutically effective amount of an scFv fusion protein to a subject in need thereof. A subject in need thereof is one who has been diagnosed as having or being at risk of developing a disease or disorder that the scFv fusion protein can treat. As described herein, as scFv fusion protein includes an scFv comprising a heavy chain immunoglobulin variable domain ($V_H$) and a light chain immunoglobulin variable domain ($V_L$), or effective fragments thereof, and a ligand binding protein fused to the scFv, wherein the affinity of the scFv for a target antigen changes in response to binding of the receptor protein to a control molecule. In some embodiments, the ligand binding protein is an estrogen receptor ligand binding domain or tamoxifen-binding estrogen receptor ligand binding domain mutant.

The scFv fusion proteins are particularly suitable for use in various forms of immunotherapy, such as CAR-T therapy. Examples of types of immunotherapy include cancer immunotherapy, dendritic cell-based pump-priming, T-cell adoptive transfer, immune enhancement therapy, allergy treatment, and immunosuppression.

In some embodiments, the scFv fusion proteins (i.e., antibody switches) may be engineered and integrated into the current platform of CAR-T therapy as a core control component to regulate T cell's targeting ability to antigens of target cells and subsequently activate or deactivate an engineered T-cell in a dose-dependent manner. The scFv fusion proteins may be used for other cell-based therapy or antibody-based immunotherapy for the treatment of a disease or condition, wherein the target cell is a malignant cell.

In some embodiments, the invention provides a method of treating cancer in a subject. In some embodiments, when the scFv is used to treat cancer, the scFv protein specifically binds to a tumor-associated antigen. The term "cancer" refers to a proliferative disorder caused or characterized by a proliferation of cells which have lost susceptibility to normal growth control. Cancers of the same tissue type usually originate in the same tissue, and may be divided into different subtypes based on their biological characteristics. Four general categories of cancer are carcinoma (epithelial cell derived), sarcoma (connective tissue or mesodermal derived), leukemia (blood-forming tissue derived) and lymphoma (lymph tissue derived).

Methods of treating cancer by in a subject by contacting a cancer cell of the subject with an scFv fusion protein are described. The contracting step can be performed in vivo or ex vivo. The target cell can be a solid tumor cell. The disclosed chimeric virus can also be used to treat a precancer condition such as cervical and anal dysplasia, other dysplasia, severe dysplasia, hyperplasia, atypical hyperplasia, or neoplasia. Thus, the target cell can be a adenocarcinoma, hepatoblastoma, sarcoma, glioma, glioblastoma, neuroblastoma, plasmacytoma, histiocytoma, melanoma, adenoma, myeloma, bladder cancer, brain cancer, squamous cell carcinoma of the head and neck, ovarian cancer, skin cancer, liver cancer, lung cancer, colon cancer, cervical cancer, breast cancer, renal cancer, esophageal carcinoma, head and neck carcinoma, testicular cancer, colorectal cancer, prostatic cancer, or pancreatic cancer.

In some embodiments, the scFv fusion protein is included in chimeric antigen receptor included in a T-cell. The scFv fusion protein can function as a core control component of the chimeric antigen receptor. An advantage of using an scFv fusion protein (e.g., the ERT2-scFv antibody switch platform) is that it may be compatible with the existing CAR-T and cell-based therapy, which use the scFv as a component of their antigen receptors. The scFv antibody switches are engineered variants of scFv; thus, the use of scFv switch in placement of the scFv in the chimeric antigen receptor domain of CAR-T may cause less functional and structural variation than other non-scFv switch mechanisms may cause while maintaining its therapeutic activity against target cells, together with a small molecule regulation feature.

In some embodiments, the advantage of using an ERT2 for the input domain is that the ERT2 binds existing FDA-approved molecules, tamoxifen, which is currently used as drug for cancer. While the native ER-LBD binds both estrogen as agonist and tamoxifen as antagonist, its mutated forms, such as including ERT0, ERT1, and ERT2, only bind tamoxifen; thus, ERT2-scFv antibody switch can be effectively controlled by administration of tamoxifen or its related analog molecules without interference with endogenously generated estrogen hormone molecules in human body.

Also, the ERT2 has been shown to be 10 times more sensitive to tamoxifen binding in vivo than ER-LBD has 22; thus, it may allow a low dose of input molecules to regulate ERT2-scFv antibody switch and subsequently to control engineered T cells in cell-based therapy. Tamoxifen or its related analogs may be administered orally or by intravenous injection to control the activity of T cell in dose dependent manner. In addition, the ERT2 is a fragment of human estrogen receptor protein, which may cause no immunogenic response to patients when used in cell-based immunotherapy.

Formulation and Administration

In certain embodiment, a composition, e.g., a pharmaceutical composition, is provided containing at least one scFv fusion protein described herein together with a pharmaceutically acceptable carrier. In one embodiment, the composition includes a combination of multiple (e.g., two or more) fusion proteins described herein. The scFv pharmaceutical composition is suitable for administration to a subject.

As described in detail below, the pharmaceutical compositions disclosed herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous, intrathecal, intracerebral or epidural injection as, for example, a sterile solution or suspension, or sustained-release formulation.

Methods of preparing these formulations or compositions include the step of bringing into association a fusion protein described herein with the carrier and, optionally, one or more accessory ingredients. In general, the formulations are prepared by uniformly and intimately bringing into association a fusion protein described herein with liquid carriers, or finely divided solid carriers, or both, and then, if necessary, shaping the product.

Pharmaceutical compositions suitable for parenteral administration comprise one or more fusion proteins described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening fusion proteins.

Examples of suitable aqueous and nonaqueous carriers which may be employed in the pharmaceutical compositions include water, ethanol, dimethyl sulfoxide (DMSO), polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The following examples are included for purposes of illustration and are not intended to limit the scope of the invention.

EXAMPLES

Example 1: Methods of Making Single Chain Variable Fragment (scFv) Fusion Proteins Strain and Reagents All chemicals and culture media used were purchased from Abcam (Cambridge, United Kingdom), BioWorld (Dublin, Ohio), Fisher Scientific (Hampton, N.H.), Millipore Sigma (Burlington, Mass.), and Sigma Aldrich (St Louis, Mo.) unless otherwise noted. Oligonucleotides were purchased from Integrated DNA Technologies (Coralville, Iowa). *E. coli* BL21(DE3) and NEB 5-alpha competent cells, and all enzymes were purchased from New England Biolabs. Plasmids pET22b+ purchased from Millipore Sigma was used as a template plasmid DNA to make fusion of the ERT2 and scFv genes. The genes of anti-CD19-scFv, anti-Her2-scFv, and ERT2 were custom synthesized by Genewiz (South Plainfield, N.J.). DNA sequencing of the regions containing the targeted codon confirmed mutant clones by Genewiz (South Plainfield).

Molecular Modeling of ERT2-scFv Fusion Proteins

The molecular models of ERT2-scFv fusion proteins were constructed with the amino acid sequence and coordinates of estrogen receptor ligand binding domain (PDB ID: 1A52 for apo, ligand-unbound conformation and 3ERT for ligand-bound conformation) and anti-Her2 scFv (PDB ID: 1N8Z was used for scFv targeting human Her2 protein and its fragment), using commercially available molecular modeling computer software, ROSETTA. Das, R. & Baker, D. Annu Rev Biochem 77, 363-382 (2008) ERT2 was a mutated form of estrogen receptor ligand binding domain with G400V/M543A/L544A mutations. These mutations were introduced to construct ERT2 model using ROSETTA. Anti-Her2 scFv model was constructed using the light chain, $V_L$ (chain A: residues 1-107) and heavy $V_H$ (chain B: residues 1-119) with a linker modeled using the Missing Loop Modeling protocol of ROSETTA with a commonly used scFv linker, $(GGGGS)_4$(SEQ ID NO: 13), to produce a single chain peptide ($V_L$: 1-107, Linker: 108-127, $V_H$: 128-246). For construction of fusion protein of ERT2 and anti-Her2-scFv, a series of input domain variants was prepared by incrementally truncating the residues L306-H550 to T311-E545 of ERT2 to generate input domain variants. The prepared ERT2 input domains were inserted into the loop-modeled scFv using the Domain Insertion protocol of ROSETTA. Both N- and C-terminal connecting regions were further optimized by repeating steps of residue mutation and refinement to produce best scoring models for a comparative analysis. The side-chain positions of the models were subsequently optimized, and the final models were optimized by energy minimization. RMSD of the scFv domain was calculated for the final models of each variant against the original structure of anti-Her2-scFv. For molecular model construction of ERT2 and anti-CD19-scFv fusion proteins, the scFv domain of the ERT2-anti-Her2-scFv fusion construct model was replaced with anti-CD19-scFv domain (PDB ID: 1YNT was used as a template for anti-CD19-scFv targeting human CD19).

Plasmids Construction

The DNA gene sequences of the computationally designed ERT2-scFv fusion proteins and variants with glycine linkers were custom synthesized from commercially available DNA synthesis service vendor (Table 1). The synthesized genes were cloned into pET22b+ plasmid, a commercially available expression vector system for protein production. ERT2-scFv fusion genes were inserted into BamHI and XhoI restriction enzyme sites of the multiple cloning sites. The insertion site was located downstream of pelB signal sequence and upstream of His-Tag (6× His) sequence, which were provided in the pET22b+ plasmid vector such that the pelB and His-Tag sequence were added to the N-terminal and C-terminal end of the fusion gene respectively.

EDTA, pH 8.0) with protease inhibitor and lysed. Cell lysates were centrifuged at 14,000 g for 1 hour to collect periplasmic fraction. EDTA trace in solution was removed by ultra-centrifugation using Amicon Ultra filter unit. The soluble proteins were purified using a commercially available Ni-NTA purification system. The purified ERT2-scFv fusion proteins were quantified using bicinchoninic acid (BCA) protein assay kit.

Evaluation for Tamoxifen Regulated Antigen-Binding Activity of ERT2-scFv Fusion Proteins For ELISA characterization of ERT2-scFv fusion proteins, a target antigen, Her2 or CD19 was purchased from commercially available vendor. Tamoxifen and its related analog such as 4-hydroxytamoxifen (4-HT) were used as small molecules to regulated antigen binding activity of ERT2-scFv fusion proteins. The multi-well plates were coated with target antigens in PBS overnight at 4° C., and incubated with blocking buffer for two hours with 4% bovine serum albumin in PBS. Purified proteins samples of ERT2-scFv variants in the absence and presence of small molecules (Tamoxifen/4-HT) were added to the antigen-coated plates and incubated for 2 hours at room temperature. After 3 rounds of washing the plates, HRP-conjugated anti-His antibody purchased from the commercially available vendor were added to the plates and incubated for 1

TABLE 1

Fusion proteins composed of ERT2 and anti-Her2-scFv/anti-CD19-scFv.

| Name* | Description** |
|---|---|
| Ert2H2 | (HER2VL: D1-K107)-(ERT2: T311-A546)-(HER2VH: E1-S119) |
| Ert2H2-G11 | (HER2VL: D1-K107)-$(G)_1$-(ERT2: T311-A546)-$(G)_1$-(HER2VH: E1-S119) |
| Ert2H2-G12 | (HER2VL: D1-K107)-$(G)_1$-(ERT2: T311-A546)-$(G)_2$-(HER2VH: E1-S119) |
| Ert2H2-G13 | (HER2VL: D1-K107)-$(G)_1$-(ERT2: T311-A546)-$(G)_3$-(HER2VH: E1-S119) |
| Ert2H2-G14 | (HER2VL: D1-K107)-$(G)_1$-(ERT2: T311-A546)-$(G)_4$-(HER2VH: E1-S119) |
| Ert2H2-G21 | (HER2VL: D1-K107)-$(G)_2$-(ERT2: T311-A546)-$(G)_1$-(HER2VH: E1-S119) |
| Ert2H2-G22 | (HER2VL: D1-K107)-$(G)_2$-(ERT2: T311-A546)-$(G)_2$-(HER2VH: E1-S119) |
| Ert2H2-G23 | (HER2VL: D1-K107)-$(G)_2$-(ERT2: T311-A546)-$(G)_3$-(HER2VH: E1-S119) |
| Ert2H2-G24 | (HER2VL: D1-K107)-$(G)_2$-(ERT2: T311-A546)-$(G)_4$-(HER2VH: E1-S119) |
| Ert2H2-G31 | (HER2VL: D1-K107)-$(G)_3$-(ERT2: T311-A546)-$(G)_1$-(HER2VH: E1-S119) |
| Ert2H2-G32 | (HER2VL: D1-K107)-$(G)_3$-(ERT2: T311-A546)-$(G)_2$-(HER2VH: E1-S119) |
| Ert2H2-G33 | (HER2VL: D1-K107)-$(G)_3$-(ERT2: T311-A546)-$(G)_3$-(HER2VH: E1-S119) |
| Ert2H2-G34 | (HER2VL: D1-K107)-$(G)_3$-(ERT2: T311-A546)-$(G)_4$-(HER2VH: E1-S119) |
| Ert2H2-G41 | (HER2VL: D1-K107)-$(G)_4$-(ERT2: T311-A546)-$(G)_1$-(HER2VH: E1-S119) |
| Ert2H2-G42 | (HER2VL: D1-K107)-$(G)_4$-(ERT2: T311-A546)-$(G)_2$-(HER2VH: E1-S119) |
| Ert2H2-G43 | (HER2VL: D1-K107)-$(G)_4$-(ERT2: T311-A546)-$(G)_3$-(HER2VH: E1-S119) |
| Ert2H2-G44 | (HER2VL: D1-K107)-$(G)_4$-(ERT2: T311-A546)-$(G)_4$-(HER2VH: E1-S119) |
| Ert2H2-G64 | (HER2VL: D1-K107)-$(G)_6$-(ERT2: T311-A546)-$(G)_4$-(HER2VH: E1-S119) |
| Ert2C19 | (CD19VL: D1-K107)-(ERT2: T311-A546)-(CD19VH: Q1-S119) |
| Ert2C19-G21 | (CD19VL: D1-K107)-$(G)_2$-(ERT2: T311-A546)-$(G)_1$-(CD19VH: Q1-S119) |
| Ert2C19-G43 | (CD19VL: D1-K107)-$(G)_4$-(ERT2: T311-A546)-$(G)_3$-(CD19VH: Q1-S119) |
| Ert2C19-G64 | (CD19VL: D1-K107)-$(G)_6$-(ERT2: T311-A546)-$(G)_4$-(CD19VH: Q1-S119) |

*G[nn] where n is the number of glycine in the N-terminal and C-terminal linker.

**HER2VL: anti-Her2 scFv light chain; HER2VH: anti-Her2 scFv heavy chain; CD19VL: anti-CD19 scFv light chain; CD19VH: anti-CD19 scFv heavy chain.

Expression and Purification of ERT2-scFv Fusion Proteins

ERT2-scFv fusion proteins with C-terminal His-Tag were expressed and purified from BL21(DE3), commercially available bacterial cells grown in M9 minimal media containing ammonium chloride (19 mM), thiamine (0.5 μg/mL), $MgSO_4$ (1 mM), $CaCl_2$ (0.1 mM), 2% glucose (w/v), 2% glycerol, Ampicillin (100 μg/mL). For production of each protein, 1 L of minimal media was inoculated with overnight culture of cells, harboring the plasmid encoding the proteins, and shaken at 37° C. until the $OD_{600}$ reached 0.7. The culture was induced with 0.5 mM isopropyl-β-D-thiogalactopyranoside (IPTG) and incubated at 23° C. for another 24 hours. After expression, the cells were harvested and resuspended in TSE buffer (50 mM Tris-HCl, 20% sucrose, and 1 mM hour at room temperature. After another six rounds of subsequent washing, tetramethyl benzene (TMB) substrate was added to each well and developed at room temperature. After 10 minutes of incubation, sulfuric acid was added to stop the reaction. Absorption was measured using a SpectraMax spectrophotometer microplate reader (Molecular Devices, Sunnyvale, Calif.). The average binding affinity of ERT2-scFv fusion variants against their target antigens in the presence and absence of small molecule was calculated from three independent trials. The switching ratio of antigen binding activity in the presence of small molecule to that in the absence of small molecule was determined for each ERT2-scFv fusion variant. The relative Kd was determined from the equation: $Y=B_{max}\times X/(Kd+X)$, and it was then normalized with Kd value of the wild type scFv.

Example 2: Modeling and Evaluation of the ERT2-scFv Antibody Switch

Strategy for the Creating of a Tamoxifen-Regulated scFv Antibody Switch System

Small molecule regulated scFv antibody was created by fusion of a scFv and a ERT2, a mutant form of estrogen receptor domain. The ERT2 was engineered to bind tamoxifen and its analog molecules via large conformation change of its structure, known as allosteric mechanism (FIG. 1). The allostery is believed to have a role in switching "on" and "off" of the activity of an output domain when it was fused to the input domain. There has been allosteric protein switches created by fusing two unrelated protein domains in such a way that the activity of the output domain is regulated by the input domain's recognition of an input signal. The random domain insertion strategy, which is based on DNA manipulation and selection, has been shown to be an effective method of establishing this coupling of activities. Previously, the domain insertion method combined with other genetic manipulation strategies has been used to create protein switches with large difference in activity between their "on" and "off" states. Guntas, G. & Ostermeier, M, J Mol Biol 336, 263-273 (2004); Guntas et al., Proc Natl Acad Sci USA 102:11224-11229 (2005); Wright et al., Proc Natl Acad Sci USA 108, 16206-16211 (2011); Nicholes, N. et al. Protein Eng Des Sel 29, 77-85 (2016) The random domain insertion strategy requires a suitable selection or screen of the large number of variants created by random genetic mutations, which is necessary to identify those fusions that show switching behavior from a combinatorial library of fusion genes encoding two domains. The size of combinatorial library is often ranged from thousands to millions fusion variants. Thus, identifying the fusions that have desired activity from a large size of library is often the most critical process; however, the required selection or screen test is not always available for proteins to be created and it has been the most challenging process with the current technology.

For creation of ERT2-scFv fusions, a computational approach of structure modeling for domain insertion was used to predict the most likely active domain fusion proteins that can work as protein switches via allosteric mechanism by calculating with measures of physic-chemical properties of the protein structure and conformation (FIGS. 4 & 5). Commercially available computer software such as ROSETTA provides tools to develop methods for generating domain fusion models with prediction scores for narrowing down to most likely active switches. ERT2 was selected as the input domain inserted into scFv domain to control target antigen binding activity of scFv against Her2 and CD19 for the following reasons: 1) ERT2 is an engineered mutant form of estrogen receptor ligand binding domain, which has been designed to bind tamoxifen and its analog while it has very low binding for estrogen, the natural ligand of estrogen receptor. Tamoxifen has been proven to be an effective and safe FDA approved, anti-cancer drug molecule; thus, it is an ideal candidate for controlling scFv to be used as a controlling component of the immunotherapeutic engineered T-cell for cancer and related diseases; 2) ERT2 domain goes thru a large conformational change upon tamoxifen binding and adapts antagonist-bound conformation, and it has been proved to be effective input domain for creating protein switches. Oakes, B. L. et al. Nat Biotechnol 34, 646-651 (2016) A large conformational change of the input domain often leads to broad and dynamic range of activity of the output domain when it is fused together. Meanwhile scFv was used for targeting disease related antigens since it is the smallest unit of immunoglobulin with full antigen-binding activity while it can be easily made in large quantity using bacterial protein expression system, allowing protein engineering and testing relatively easy and fast that being done in mammalian expression system.

Computational Modeling of a Tamoxifen-Activated ERT2-scFv

To build structural models for ERT2-scFv fusion proteins, coordinates for crystal structures of ligand bound and unbound state of estrogen receptor ligand binding domain, anti-Her2-scFv, and anti-CD19-scFv were used. First, the ERT2 structure was created from estrogen receptor ligand binding domain structure by introducing designated amino acid mutations: G400V/M543A/L544A. The incrementally truncated variants of the ERT2 input domain was then inserted into various sites along the connecting region between the light and heavy chain of scFv domain. Since ERT2 was expected to undergo conformational change upon ligand recognition, both ligand unbound and bound state structures were used to build ERT2-scFv fusion structure models for both "off" and "on" state. The candidate models with the most disruption of antigen binding site in "off" state and the most well conserved antigen binding site in "on" state were chosen for review. The final structure models of ERT2-scFv fusion showed that the ligand unbound conformation of ERT2 disrupted scFv variable chins to be in an inactive form while tamoxifen-binding induced conformational change and re-assembled the light and heavy chain of scFv to form an active antigen-binding sites (FIG. 5). In this final fusion models, N-terminal residues from 306 to 310 and C-terminal residues from 547 to 550 of ERT2 domain were truncated. The truncated ERT2 was inserted between in the C-terminal region of light chain and N-terminal region of heavy chain of anti-Her2-scFv. This model was then used to create a fusion protein, Ert2H2 for evaluation (Table 1).

Active Control of Target Antigen Binding of scFv with Small Molecule

In order to test Ert2H2's ability to act as tamoxifen-regulated scFv antibody, Ert2H2 protein was constructed and evaluated. The gene that encodes Ert2H2 was synthesized with BamHI and XhoI restriction digestion sites included at the N- and C-terminal region respectively. The synthesized gene was ligated into pET22b+ plasmid in such a way that a pelB signal sequence was added to the fusion gene at the N-terminal for secretion and folding in a periplasmic environment of *E. coli* cell while a His-Tag sequence was added to the C-terminal for Ni-NTA purification. To compare Ert2H2 with the canonical antigen binding ability of anti-Her2-scFv and ERT2 in the absence and presence of tamoxifen and its analog, genes of anti-Her2-scFv and ERT2 were also synthesized and inserted into the pET22b+ using the same strategy. The genes were placed under the control of the strong inducible T7 promoter for high expression of the proteins under control of IPTG. As desired, Ert2H2, ERT2, and anti-Her2-scFv were expressed in *E. coli* BL21(DE3) cell and periplasmic proteins were extracted using osmotic shock method. The proteins were purified using Ni-NTA system and further concentrated for ELISA assay to evaluate tamoxifen dependent antigen binding activity.

Ert2H2's ability to act as a tamoxifen-regulated scFv antibody targeting against Her2 antigen was evaluated using ELISA assay in the absence and presence of tamoxifen analog, 4-HT. The ELISA assay was performed to evaluate Ert2H2's selective binding against Her2 antigen in the series of concentration of 4-HT. Anti-Her2-scFv and ERT2 were used as used as positive and negative controls respectively. In the Her2 binding characterization in the absence and presence of 4-HT, Ert2H2 showed 4-HT-dose-dependent Her2 binding activity with ~11 fold change in activity in the absence and presence of the ligand (Table 2). Ert2H2 therefore represents a switchable scFv antibody.

TABLE 2

4-HT dependent antigen binding affinity and switching ratio of Ert2H2.

| Construct | Relative $K_d$ (nM)[a] −(4-HT) | Relative $K_d$ (nM)[a] +(4-HT) | Normalized affinity[b] −(4-HT) | Normalized affinity[b] +(4-HT) | Switching Ratio[c] |
|---|---|---|---|---|---|
| Anti-Her2-scFv | 0.11 ± 0.06 | 0.10 ± 0.03 | 1.00 | 1.00 | 1.0 |
| Ert2H2 | 73.54 ± 0.74 | 6.38 ± 0.12 | 0.0015 | 0.016 | 10.7 |

[a]The relative $K_d$ was determined from one site-specific binding fitting.
[b]The normalized binding affinity was calculated with anti-Her2-scF.
[c]The switch ratio is a ratio of binding affinity in the presence of 4-HT to that in the absence of 4-HT.

scFv Antigen Targeting Activity is Controlled by Ligand-Specific Binding of 4-HT to ERT2 Input Domain with the Antagonist ERT2 Conformation.

Ert2H2 also showed discrimination with 4-HT against β-estradiol, which supports the initial hypothesis that Ert2H2 is able to transduce ligand-specific binding of 4-HT into scFv antigen target binding activity through the antagonist conformation rather than the agonist conformation with β-estradiol as shown in the previous work (Table 3). In addition, the low background binding activity suggests that an insertion of ERT2 domain mostly disrupts the antigen-binding site until it is recovered by ligand binding, and this can be adapted for tight control of target antigen recognition.

TABLE 3

β-estradiol dependent antigen binding affinity and switching ratio of Ert2H2.

| Construct | Relative $K_d$ (nM)[a] −(β-estradiol) | Relative $K_d$ (nM)[a] +(β-estradiol) | Normalized affinity[b] −(β-estradiol) | Normalized affinity[b] +(β-estradiol) | Switching Ratio[c] |
|---|---|---|---|---|---|
| Anti-Her2-scFv | 0.09 ± 0.04 | 0.12 ± 0.04 | 1.00 | 1.00 | 1.0 |
| Ert2H2 | 65.28 ± 0.87 | 69.98 ± 0.15 | 0.0013 | 0.0017 | 1.3 |

[a]The relative $K_d$ was determined from one site-specific binding fitting.
[b]The normalized binding affinity was calculated with anti-Her2-scFv.
[c]The switch ratio is a ratio of binding affinity in the presence of β-estradiol to that in the absence of β-estradiol.

Optimization of Control Range for scFv Binding Activity with Variable Length Linker To improve Ert2H2 control, we sought to optimize the linker region that connects input and out domain to increase switching ratio of target antigen binding affinity in the absence and presence of the input ligand. We designed a set of linkers with varying number of glycine from one to six residues with up to three residues difference between N- and C-terminal linkers based on structure review of Ert2H2 fusion models. The designed variable linkers were inserted into N- and C-terminal connecting sites of ERT2 to scFv domain (Table 1). ELISA binding assay showed two and four glycines in the N-terminal linker and one and three glycines in the C-terminal linker with one residue difference between linkers showed increased ligand-dependent switch ratio from 10.7 fold to 34.8 fold for Ert2H21 and 55.1 fold for Ert2H43 (Table 4). The switching was improved by having increased binding affinity in the presence of 4-HT since the background level in the absence of 4-HT remained similar. This shows that the linker optimization strategy improved switching by improving "ON" state rather reducing "OFF" state, suggesting the glycine repeat linker helped correct formation of antigen binding site via improved arrangement of variable chains of scFv.

TABLE 4

An antigen binding affinity and switching ratio of Ert2H2 variants.

| Construct | Relative $K_d$ (nM)[a] −(4-HT) | Relative $K_d$ (nM)[a] +(4-HT) | Normalized affinity[b] −(4-HT) | Normalized affinity[b] +(4-HT) | Switching Ratio[c] |
|---|---|---|---|---|---|
| Anti-Her2-scFv | 0.15 ± 0.04 | 0.17 ± 0.03 | 1.00 | 1.00 | 1.0 |
| Ert2H2-G11 | 64.86 ± 5.23 | 4.46 ± 0.43 | 0.0023 | 0.038 | 16.5 |
| Ert2H2-G12 | 54.75 ± 3.94 | 5.75 ± 0.44 | 0.0027 | 0.030 | 10.8 |
| Ert2H2-G13 | 68.32 ± 6.86 | 7.29 ± 0.56 | 0.0022 | 0.023 | 10.6 |
| Ert2H2-G14 | 70.12 ± 6.04 | 5.93 ± 0.81 | 0.0021 | 0.029 | 13.4 |
| Ert2H2-G21 | 76.56 ± 4.98 | 2.49 ± 0.13 | 0.0020 | 0.068 | 34.8 |
| Ert2H2-G22 | 72.34 ± 4.03 | 3.93 ± 0.70 | 0.0021 | 0.043 | 20.9 |
| Ert2H2-G23 | 75.79 ± 6.30 | 4.74 ± 0.35 | 0.0020 | 0.036 | 18.1 |
| Ert2H2-G24 | 64.34 ± 5.25 | 3.41 ± 0.26 | 0.0023 | 0.050 | 21.4 |
| Ert2H2-G31 | 75.36 ± 6.01 | 3.78 ± 0.54 | 0.0020 | 0.045 | 22.6 |
| Ert2H2-G32 | 68.53 ± 3.72 | 3.05 ± 0.32 | 0.0022 | 0.056 | 25.5 |
| Ert2H2-G33 | 59.34 ± 2.98 | 5.76 ± 0.57 | 0.0025 | 0.030 | 11.7 |
| Ert2H2-G34 | 53.67 ± 1.25 | 4.18 ± 0.41 | 0.0028 | 0.041 | 14.6 |
| Ert2H2-G41 | 71.16 ± 7.87 | 5.42 ± 0.73 | 0.0021 | 0.031 | 14.9 |
| Ert2H2-G42 | 64.93 ± 3.37 | 3.10 ± 0.29 | 0.0023 | 0.055 | 23.7 |
| Ert2H2-G43 | 61.76 ± 6.66 | 1.27 ± 0.15 | 0.0024 | 0.134 | 55.1 |
| Ert2H2-G44 | 56.78 ± 1.24 | 5.48 ± 0.42 | 0.0026 | 0.031 | 11.7 |
| Ert2H2-G64 | 48.25 ± 1.96 | 2.01 ± 0.79 | 0.0031 | 0.085 | 27.2 |

[a]The relative $K_d$ was determined from one site-specific binding fitting.
[b]The normalized binding affinity was calculated with the wild-type scFv: anti-Her2-scF.
[c]The switch ratio is a ratio of binding affinity in the presence of 4-HT to that in the absence of 4-HT.

Modularity of ERT2-scFv Antibody Switch

Single-chain variable fragment (scFv) is the smallest functional antibody form that still contains full antigen-binding site and targeting ability. scFv was selected as the antigen binding output domain for the presently disclosed engineered small molecule regulated scFv antibody switch system due to antigen binding modularity of scFv structure. While scFv domain maintains its structural topology and arrangement, the mutations at antigen binding site formed by variable chains results in antigen binding specificity. Our computational modeling suggests that Ert2H2 and its variants would share the same modularity of scFv domain; thus it allows development of ERT2-scFv antibody switch that targets different antigen by simply replacing the output domain.

To test the modularity of the presently disclosed system, the scFv domain of Ert2H2-G2, Ert2H2-G43, and Ert2H2-G64 were replaced with anti-CD19-scFv targeting human CD19 to create Ert2C19-G21, Ert2C19-G43, and Ert2C19-G64, respectively. The human CD19 antigen is a type I transmembrane glycoprotein and a biomarker for normal and neoplastic B cells. CD19 is critically involved in establishing intrinsic B cell signaling thresholds through modulating both B cell receptor-dependent and independent signaling. Especially, CD19 has been used in CD19-targeted therapies based on T cells that express CD19-specific chimeric antigen receptors (CARs), which have been utilized for the cancer treatment with CD19+ lymphoma and leukemia.

The light and heavy chain of Ert2H2 were replaced with residue 1-107 and 1-119 of the light and heavy chain from anti-CD19-scFv while ERT2 domain and linkers were remained the same. Tamoxifen-dependent antigen binding was characterized again with ELISA in the absence and presence of 4-HT. Both Ert2C19-G21, Ert2C19-G43, and Ert2C19-G64 constructs showed 25.7 fold, 38.3 fold, and 22.79 fold switching activity respectively (Table 5). The switch ratios were slightly lower than those of Ert2H2 constructs. The lower switching activity can be contemplated since two constructs were optimized variants for Ert2H2 targeting Her2 antigen. However, these results indicate that the modular ERT2-scFv platform has the potential to be redesigned and engineered to target a wide range of antigen with small molecule control.

TABLE 5

An antigen binding affinity and switching ratio of Ert2C19 variants.

| Construct | Relative $K_d$ (nM)[a] −(4-HT) | Relative $K_d$ (nM)[a] +(4-HT) | Normalized affinity[b] −(4-HT) | Normalized affinity[b] +(4-HT) | Switching Ratio[c] |
|---|---|---|---|---|---|
| Anti-CD19-scFv | 0.56 ± 0.02 | 0.49 ± 0.05 | 1.00 | 1.00 | 1.0 |
| Ert2C19-G21 | 63.48 ± 5.39 | 2.16 ± 0.19 | 0.0088 | 0.2269 | 25.7 |
| Ert2C19-G43 | 54.75 ± 7.10 | 1.25 ± 0.14 | 0.0102 | 0.392 | 38.3 |
| Ert2C19-G64 | 51.83 ± 4.04 | 1.99 ± 0.12 | 0.0108 | 0.246 | 22.79 |

[a]The relative $K_d$ was determined from one site-specific binding fitting.
[b]The normalized binding affinity was calculated with anti-CD19-scFv.
[c]The switch ratio is a ratio of binding affinity in the presence of 4-HT to that in the absence of 4-HT.

Example 3: Discussion of the ERT2-scFv Antibody Switch

Remote control of targeting ability of scFv antibody against a wide range of antigens can be a powerful key component for engineering cell-based immunotherapeutic system. In addition, modular architecture of the controllable scFv component may provide a means to regulate the immune system with a choice of molecules that can be applicable to different cellular or biological environment.

In this work, we took advantage of computational design and modeling to create fusions of a mutated form of estrogen receptor ligand binding domain and scFv, and performed only a small-scale optimization to develop an effective tamoxifen-regulated scFv that could target Her2 or CD19 in dose-dependent fashion. The initial computational design was based on the assumption that tamoxifen-regulated switching could occur via an allosteric signal transduced by the conformational change of ERT2 upon ligation binding. Ert2H2 and Ert2C19 variants showed their ligand-dependent antigen binding function as our initial design predicted. Although we do not have a direct evidence of molecular dynamics of the mechanism, it can be contemplated based on the current switching activity results and modeling hypothesis that Ert2H2 and Ert2C19 switch variants adapts a non-functional form of scFv domain disrupted by ERT2 domain insertion in the absence of the ligand. Then, the ligand binding transduces allosteric signal via conformational change to revert the antigen binding activity of scFv domain by rearranging the light and heavy chain (FIG. 5).

While the correct arrangement of variable light and heavy chain is important in formation of antigen binding site and in controlling binding affinity, the flexible peptide linker that connects the variable chains plays an important role in maintaining the delicate inter-domain interaction and consequently the antigen binding ability. A slight change of this linker may dramatically increase or decrease the target antigen recognition. Padlan, E. A., Mol Immunol, 31(3): p. 169-217 (1994); Huston, J. S., et al., Proc Natl Acad Sci USA, 85(16): p. 5879-83 (1988). Meanwhile, protein switch engineering has shown that the length and nature of inter-domain linker is critical for adapting switch function from domain insertion. There must meet delicate balance between uncoupling of structure and maintaining a correct fold with optimum length and context of a linker. Cutler, T. A., et al., J Mol Biol, 386(3): p. 854-68 (2009). These similar criteria for the linker that applies to both scFv's target recognition ability and protein switch's switching activity encourage careful optimization of Ert2H2 as this linker variation can lead to improvement of both antigen recognition and switching activity. While both Ert2H2-G21 and Ert2H-G43 showed increased level of antigen recognition that subsequently improve switching ratio in the absence and presence of the ligand, further optimization may lead to even more improved switching and control activity in the future.

One of the desired properties of protein switches is a modular architecture that allows simple redesign and engineering to change either its controlling input molecule or output signal. While it is theoretically possible to redesign the structure of both input and output domain to act as a universal switch, the physicochemical properties of protein structure mostly limits its interacting molecules to specific group of proteins or molecules of few. The previous studies had demonstrated that it was possible to convert a ligand binding site of one protein to recognize other molecules with high specificity and selectivity. However, the current technology is still limited to redesign and engineering of a specific group of proteins to recognize a small range of molecules and it often requires a rigorous work of combinatorial library creation and selection only if the suitable selection is available. The recent development of de novo computational protein design shows prospect of creating proteins with any desired properties, but it still has shown limited success to small group of molecules. Our ERT2-scFv antibody switch platform has an advantage of converting output domain to interact with different target antigen owing to its unique nature of variable chains forming a binding site that allows targeting a wide range of different antigens with mutations while maintaining structural arrangements. We converted ERT2-scFv antibody switches that recognize Her2 to those that recognize CD19 by replacing the scFv domain, showing slightly lower switch ratio for antigen binding activity with tamoxifen analogs. The current results showed modularity of an output domain; yet converting an input domain to do bind different controlling input molecules will require more extensive combinatorial mutagenesis at ligand binding sites. Future work of the ERT2-scFv antibody switches will focus on combinatorial library creation and selection to convert input domain to bind a range of molecule to be used as controlling molecules.

The recent development and application of immunotherapy and CAR-T technology has revolutionized cancer therapeutic development and cell-based therapy. However, a better control of engineered cells is much needed in order to further advance the current stage of cell-based immunotherapy. Precise dose control and timing, and monitoring and reducing side effect have been limited by its nature of cell therapy with little control of cell proliferation once injected. We therefore developed tamoxifen, a FDA-approved anti-cancer drug molecule, regulated ERT2-scFv antibody switch protein that can be integrated into engineered T-cells to be used as a control component of CAR-T or other engineered cell in cell based immunotherapy.

Example 4: Representative Sequences

Protein Sequence of the ERT2scFv

Ert2H2

(SEQ ID NO: 6)

DIQMTQSPSSLSASVGDRVTITCRASQDVNTAVAWYQQKPGKAPKLLIYSASF

LYSGVPSRFSGSRSGTDFTLTISSLQPEDFATYYCQQHYTTPPTFGQGTKVEIKTADQ

MVSALLDAEPPILYSEYDPTRPFSEASMMGLLTNLADRELVHMINWAKRVPGFVDLT

LHDQVHLLECAWLEILMIGLVWRSMEHPVKLLFAPNLLLDRNQGKCVEGMVEIFDM

LLATSSRFRMMNLQGEEFVCLKSIILLNSGVYTFLSSTLKSLEEKDHIHRVLDKITDTLI

HLMAKAGLTLQQQHQRLAQLLLILSHIRHMSNKGMEHLYSMKCKNVVPLYDLLLE

AADAEVQLVESGGGLVQPGGSLRLSCAASGFNIKDTYIHWVRQAPGKGLEWVARIY

PTNGYTRYADSVKGRFTISADTSKNTAYLQMNSLRAEDTAVYYCSRWGGDGFYAM

DYWGQGTLVTVSLEHHHHHH

Ert2H2-G21

(SEQ ID NO: 7)

DIQMTQSPSSLSASVGDRVTITCRASQDVNTAVAWYQQKPGKAPKLLIYSASF

LYSGVPSRFSGSRSGTDFTLTISSLQPEDFATYYCQQHYTTPPTFGQGTKVEIKGGTA

DQMVSALLDAEPPILYSEYDPTRPFSEASMMGLLTNLADRELVHMINWAKRVPGFV

DLTLHDQVHLLECAWLEILMIGLVWRSMEHPVKLLFAPNLLLDRNQGKCVEGMVEI

FDMLLATSSRFRMMNLQGEEFVCLKSIILLNSGVYTFLSSTLKSLEEKDHIHRVLDKIT

DTLIHLMAKAGLTLQQQHQRLAQLLLILSHIRHMSNKGMEHLYSMKCKNVVPLYDL

LLEAADAGEVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYCSRWGGDGF

YAMDYWGQGTLVTVSLEHHHHHH

Ert2H2-G43

(SEQ ID NO: 8)

DIQMTQSPSSLSASVGDRVTITCRASQDVNTAVAWYQQKPGKAPKLLIYSASF

LYSGVPSRFSGSRSGTDFTLTISSLQPEDFATYYCQQHYTTPPTFGQGTKVEIKGGGG

TADQMVSALLDAEPPILYSEYDPTRPFSEASMMGLLTNLADRELVHMINWAKRVPG

FVDLTLHDQVHLLECAWLEILMIGLVWRSMEHPVKLLFAPNLLLDRNQGKCVEGM

VEIFDMLLATSSRFRMMNLQGEEFVCLKSIILLNSGVYTFLSSTLKSLEEKDHIHRVLD

KITDTLIHLMAKAGLTLQQQHQRLAQLLLILSHIRHMSNKGMEHLYSMKCKNVVPL

YDLLLEAADAGGGEVQLVESGGGLVQPGGSLRLSCAASGFNIKDTYIHWVRQAPGK

GLEWVARIYPTNGYTRYADSVKGRFTISADTSKNTAYLQMNSLRAEDTAVYYCSRW

GGDGFYAMDYWGQGTLVTVSLEHHHHHH

Ert2C19-G21

(SEQ ID NO: 9)

DIQMTQTTSSLSASLGDRVTISCRASQDISKYLNWYQQKPDGTVKLLIYHTSR

LHSGVPSRFSGSGSGSGTDYSLTISNLEQEDIATYFCQQGNTLPYTFGGGTKLEITGGTA

DQMVSALLDAEPPILYSEYDPTRPFSEASMMGLLTNLADRELVHMINWAKRVPGFV

DLTLHDQVHLLECAWLEILMIGLVWRSMEHPVKLLFAPNLLLDRNQGKCVEGMVEI

FDMLLATSSRFRMMNLQGEEFVCLKSIILLNSGVYTFLSSTLKSLEEKDHIHRVLDKIT

-continued

DTLIHLMAKAGLTLQQQHQRLAQLLLILSHIRHMSNKGMEHLYSMKCKNVVPLYDL

LLEAADAGEVKLQESGPGLVAPSQSLSVICTVSGVSLPDYGVSWIRQPPRKGLEWLG

VIWGSETTYYNSALKSRLTIIKDNSKSQVFLKMNSLQTDDTAIYYCAKHYYYGGSYA

MDYWGQGTSVTVSSLEHHHHHH

Ert2C19-G43

(SEQ ID NO: 10)

DIQMTQTTSSLSASLGDRVTISCRASQDISKYLNWYQQKPDGTVKLLIYHTSR

LHSGVPSRFSGSGSGTDYSLTISNLEQEDIATYFCQQGNTLPYTFGGGTKLEITGGGGT

ADQMVSALLDAEPPILYSEYDPTRPFSEASMMGLLTNLADRELVHMINWAKRVPGF

VDLTLHDQVHLLECAWLEILMIGLVWRSMEHPVKLLFAPNLLLDRNQGKCVEGMV

EIFDMLLATSSRFRMMNLQGEEFVCLKSIILLNSGVYTFLSSTLKSLEEKDHIHRVLDK

ITDTLIHLMAKAGLTLQQQHQRLAQLLLILSHIRHMSNKGMEHLYSMKCKNVVPLY

DLLLEAADAGGGEVKLQESGPGLVAPSQSLSVTCTVSGVSLPDYGVSWIRQPPRKGL

EWLGVIWGSETTYYNSALKSRLTIIKDNSKSQVFLKMNSLQTDDTAIYYCAKHYYYG

GSYAMDYWGQGTSVTVSSLEHHHHHH

Ert2H2-G64

(SEQ ID NO: 11)

DIQMTQSPSSLSASVGDRVTITCRASQDVNTAVAWYQQKPGKAPKLLIYSASF

LYSGVPSRFSGSRSGTDFTLTISLQPDFATYYCQQHYTTPPTFGQGTKVEIKGGGG

GGTADQMVSALLDAEPPILYSEYDPTRPFSEASMMGLLTNLADRELVHMINWAKRV

PGFVDLTLHDQVHLLECAWLEILMIGLVWRSMEHPVKLLFAPNLLLDRNQGKCVEG

MVEIFDMLLATSSRFRMMNLQGEEFVCLKSIILLNSGVYTFLSSTLKSLEEKDHIHRV

LDKITDTLIHLMAKAGLTLQQQHQRLAQLLLILSHIRHMSNKGMEHLYSMKCKNVV

PLYDLLLEAADAGGGGEVQLVESGGGLVQPGGSLRLSCAASGFNIKDTYIHWVRQA

PGKGLEWVARIYPTNGYTRYADSVKGRFTISADTSKNTAYLQMNSLRAEDTAVYYC

SRWGGDGFYAMDYWGQGTLVTVSLEHHHHHH

Ert2C19-G64

(SEQ ID NO: 12)

DIQMTQTTSSLSASLGDRVTISCRASQDISKYLNWYQQKPDGTVKLLIYHTSR

LHSGVPSRFSGSGSGSGTDYSLTISNLEQEDIATYFCQQGNTLPYTFGGGTKLEITGGGG

GGTADQMVSALLDAEPPILYSEYDPTRPFSEASMMGLLTNLADRELVHMINWAKRV

PGFVDLTLHDQVHLLECAWLEILMIGLVWRSMEHPVKLLFAPNLLLDRNQGKCVEG

MVEIFDMLLATSSRFRMMNLQGEEFVCLKSIILLNSGVYTFLSSTLKSLEEKDHIHRV

LDKITDTLIHLMAKAGLTLQQQHQRLAQLLLILSHIRHMSNKGMEHLYSMKCKNVV

PLYDLLLEAADAGGGGEVKLQESGPGLVAPSQSLSVTCTVSGVSLPDYGVSWIRQPP

RKGLEWLGVIWGSETTYYNSALKSRLTIIKDNSKSQVFLKMNSLQTDDTAIYYCAKH

YYYGGSYAMDYWGQGTSVTVSSLEHHHHHH

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A single chain variable fragment (scFv) fusion protein, comprising an scFv comprising a heavy chain immunoglobulin variable domain ($V_H$) and a light chain immunoglobulin variable domain ($V_L$), and a ligand binding protein consisting of an estrogen receptor ligand binding domain (ER-LBD) or a tamoxifen-binding estrogen receptor ligand binding domain mutant (ERT-LBD) fused to the scFv, wherein the ligand binding protein is fused between $V_H$ and $V_L$ of the scFv.

2. The fusion protein of claim 1, wherein one or more linker amino acids are included between the scFv and the ligand binding protein.

3. The fusion protein of claim 1, wherein $V_L$ comprises SEQ ID NO: 1 and $V_H$ comprises SEQ ID NO: 2.

4. The fusion protein of claim 1, wherein $V_L$ comprises SEQ ID NO: 4 and $V_H$ comprises SEQ ID NO: 5.

5. The fusion protein of claim 1, wherein the ligand binding protein is ERT0, ERT1, or ERT2.

6. The fusion protein of claim 1, wherein the ligand binding protein is an ERT-LBD polypeptide comprising SEQ ID NO: 3.

7. The fusion protein of claim 1, wherein the fusion protein comprises a peptide selected from the group consisting of SEQ ID NO: 6, SEQ ID NO: 7, SEQ ID NO: 8, SEQ ID NO: 9, SEQ ID NO: 10, SEQ ID NO: 11, and SEQ ID NO: 12.

8. A method of treating a disease or disorder comprising administering a therapeutically effective amount of the fusion protein according to claim 1 to the subject.

9. The method of claim 8, wherein the disease or disorder is cancer and the scFv specifically binds to a tumor-associated antigen.

10. The method of claim 8, wherein the fusion protein is coupled to and provides antigen-specificity to a chimeric antigen receptor present on a T-cell.

11. The method of claim 8, wherein the fusion protein is administered together with a pharmaceutically acceptable carrier.

12. A nucleic acid encoding a fusion protein according to claim 1.

13. The nucleic acid of claim 12, wherein the nucleic acid encodes a fusion protein having least 90% sequence identity to a peptide selected from the group consisting of SEQ ID NO: 6, SEQ ID NO: 7, SEQ ID NO: 8, SEQ ID NO: 9, SEQ ID NO: 10, SEQ ID NO: 11, and SEQ ID NO: 12.

* * * * *